(12) United States Patent
Cremer et al.

(10) Patent No.: US 8,025,846 B2
(45) Date of Patent: Sep. 27, 2011

(54) PROCESS FOR INTRODUCING A PORTION WITHDRAWN FROM AT LEAST ONE PRODUCTION CHARGE OF ANNULAR COATED CATALYSTS K INTO A REACTION TUBE OF A TUBE BUNDLE REACTOR

(75) Inventors: Ulrich Cremer, Mannheim (DE);
Hagen Wilmer, Ludwigshafen (DE);
Andreas Raichle, Ludwigshafen (DE);
Hermann Petersen, Gruenstadt (DE);
Holger Borchert, Offstein (DE); Horst Strahberger, Dannstadt-Schauernheim (DE); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 559 days.

(21) Appl. No.: 12/138,862

(22) Filed: Jun. 13, 2008

(65) Prior Publication Data
US 2008/0307648 A1    Dec. 18, 2008

Related U.S. Application Data

(60) Provisional application No. 60/944,327, filed on Jun. 15, 2007.

(30) Foreign Application Priority Data

Jun. 15, 2007 (DE) .................. 10 2007 028 333

(51) Int. Cl.
*B01J 35/02* (2006.01)
(52) U.S. Cl. ............ 422/131; 502/8; 502/100; 502/439; 422/310; 29/890
(58) Field of Classification Search .................. 29/890; 502/8, 100
See application file for complete search history.

(56) References Cited

U.S. PATENT DOCUMENTS

| | | | | | |
|---|---|---|---|---|---|
| 2,885,246 | A | * | 5/1959 | De Haven | 406/68 |
| 3,779,712 | A | * | 12/1973 | Calvert et al. | 422/219 |
| 4,021,599 | A | * | 5/1977 | Kochhar et al. | 526/124.9 |
| 4,077,912 | A | * | 3/1978 | Dolhyj et al. | 502/178 |
| 4,297,247 | A | * | 10/1981 | Krabetz et al. | 502/310 |
| 4,409,186 | A | * | 10/1983 | Gibson et al. | 422/131 |
| 4,622,424 | A | * | 11/1986 | Callahan et al. | 562/545 |
| 4,656,157 | A | * | 4/1987 | Hofmann et al. | 502/439 |
| 6,933,407 | B2 | * | 8/2005 | Berndt et al. | 562/549 |

* cited by examiner

*Primary Examiner* — Duane Smith
*Assistant Examiner* — Ives Wu
(74) *Attorney, Agent, or Firm* — Oblon, Spivak, McClelland, Maier & Neustadt, L.L.P.

(57) ABSTRACT

A process for introducing annular coated catalysts K into a reaction tube of a tube bundle reactor, in which adhering pairs of annular coated catalysts K formed in the preparation of the annular coated catalysts K, before the introduction thereof into the reaction tube, are removed at least partly from the annular coated catalysts K.

32 Claims, 5 Drawing Sheets

PROCESS FOR INTRODUCING A PORTION WITHDRAWN FROM AT LEAST ONE PRODUCTION CHARGE OF ANNULAR COATED CATALYSTS K INTO A REACTION TUBE OF A TUBE BUNDLE REACTOR

BACKGROUND OF THE INVENTION

The present invention relates to a process for introducing a portion withdrawn from at least one production charge of annular coated catalysts K into a reaction tube of a tube bundle reactor for the purpose of charging this reaction tube with a fixed catalyst bed suitable for performing a heterogeneously catalyzed partial gas phase oxidation of an organic starting compound.

Processes for heterogeneously catalyzed partial gas phase oxidation of organic starting compounds in fixed catalyst beds disposed in the reaction tubes of tube bundle reactors are known for the preparation of numerous industrial chemicals.

Examples of such heterogeneously catalyzed partial gas phase oxidations of organic compounds include the conversion of methanol to formaldehyde (cf., for example, CH-A 449 600 and CH-A 38 828), the conversion of propene to acrolein and/or acrylic acid (cf., for example, DE-A 23 51 151), the conversion of tert-butanol, isobutene, isobutane, isobutyraldehyde or the methyl ether of tert-butanol to methacrolein and/or methacrylic acid (cf., for example, DE-A 25 26 238, EP-A 092 097, EP-A 058 927, DE-A 41 32 263, DE-A 41 32 684 and DE-A 40 22 212), the conversion of acrolein to acrylic acid and of methacrolein to methacrylic acid (cf., for example, DE-A 25 26 238), the conversion of o-xylene and/or naphthalene to phthalic anhydride (cf., for example, EP-A 522 871) and the conversion of butadiene to maleic anhydride (cf., for example, DE-A 21 06 796 and DE-A 16 24 921), the conversion of $C_4$ hydrocarbons such as 1-butene, 2-butene, butadiene and/or n-butane to maleic anhydride (cf., for example, GB-A 14 64 198 and GB-A 12 91 354), the conversion of indanes to anthraquinones (cf., for example, DE-A 20 25 430), the conversion of ethylene to ethylene oxide (cf., for example, EP-A 352 849, EP-A 352 850, EP-A 532 325, U.S. Pat. Nos. 5,155,242 and 5,262,551) or of propylene to propylene oxide (cf., for example, DE-B 12 54 137, DE-A 21 59 346, EP-A 372 972, WO 89/07101, DE-A 43 11 608), the conversion of propylene and/or acrolein to acrylonitrile (cf., for example, DE-A 23 51 151), the conversion of isobutene and/or methacrolein to methacrylonitrile (i.e. the term "partial oxidation" shall, in this document, also comprise partial ammoxidation, i.e. a partial oxidation in the presence of ammonia), the oxidative dehydrogenation of hydrocarbons or hydrocarbon derivatives (cf., for example, DE-A 23 51 151), the conversion of propane to acrylonitrile or to acrolein and/or acrylic acid (cf., for example, DE-A 101 31 297, EP-A 10 90 684, EP-A 608 838, DE-A 100 46 672, EP-A 529 853, WO 01/96270 and DE-A 100 28 582) etc.

While a full oxidation of an organic compound with molecular oxygen is understood in this document to mean that the organic compound is converted under the reactive action of molecular oxygen such that all of the carbon present in the organic compound is converted to oxides of carbon and all of the hydrogen present in the organic compounds to oxides of hydrogen, all different exothermic conversions of an organic compound under the reactive action of molecular oxygen are summarized in this document as partial oxidations of an organic compound.

In particular, in this document, partial oxidations shall be understood to mean those exothermic conversions of organic compounds under the reactive action of molecular oxygen in which the organic compound to be oxidized partially, after the conversion has ended, comprises at least one oxygen atom more in chemically bound form than before the partial oxidation was performed.

A tube bundle reactor is normally an apparatus which comprises a vertically arranged bundle of reaction tubes which is surrounded by a reactor jacket, both ends of the individual reaction tubes being open and the upper end of each reaction tube ending sealed into a passage orifice of an upper tube plate sealed at the top into the reactor jacket and the lower end ending sealed into a passage orifice of a lower tube plate sealed at the bottom into the reactor jacket, the exterior of the reaction tubes, the upper and the lower tube plate and the reactor jacket together delimiting the reaction tube surrounding space, and each of the two tube plates being spanned by a reactor hood having at least one orifice. In the performance of a heterogeneously catalyzed partial gas phase oxidation in such a tube bundle reactor, its reaction tubes are charged with a fixed catalyst bed (a fixed catalyst bed is introduced into its reaction tubes; a fixed catalyst bed is disposed in its reaction tubes) and a reaction gas input mixture which comprises the organic compound (organic starting compound) to be oxidized partially and molecular oxygen is fed in through the at least one orifice in one of the two reactor hoods, and the product gas mixture which comprises the target product which results through partial gas phase oxidation of the organic starting compound to be oxidized partially to the desired target product as it flows through the fixed catalyst bed disposed in the reaction tubes is removed via the at least one orifice of the other reactor hood, while at least one (generally liquid) heat exchange medium is conducted around the reaction tubes on the jacket side of the tube bundle reactor. Normally, in the case of use of at least one liquid heat exchange medium, it is conducted around the reaction tubes such that each of the two surfaces of the two tube plates facing one another is wetted by liquid heat exchange medium. The at least one (for example liquid) heat exchange medium is typically conducted into the reaction tube surrounding space with a temperature $T_H^{in}$ and back out of the reaction tube surrounding space with the temperature of $T_H^{out}$.

The statement that the reaction tubes are sealed into the passage orifices in the upper and lower tube plate means that there is no means of passage for the heat exchange medium between the reaction tube outer wall and the bore wall (i.e. wall of the passage orifice or else shell of the passage orifice). Such a seal can be effected, for example, as described in DE-20 2006 014 116 U1.

In principle, the at least one heat exchange medium may also be conducted in gaseous form or in the boiling state through the reaction tube surrounding space. Examples of such tube bundle reactors and heterogeneously catalyzed partial gas phase oxidations performed therein are disclosed, for example, by EP-A 700 893, DE-A 44 31 949, WO 03/057 653, EP-A 16 95 954, WO 03/055 835, WO 03/059 857, WO 03/076 373, DE 699 15 952 T2, DE-A 10 2004 018 267, DE 20 2006 014 116 U1 and DE 10 2007 019 597.6, and also the prior art cited in the aforementioned documents.

In general, the components of the tube bundle reactor are manufactured from steel. Useful manufacturing steel is both stainless steel (for example of DIN materials number 1.4541 or 1.4571) and black steel or ferritic steel (for example DIN materials 1.0481, 1.0315 or material 1.0425). Frequently, all components of the tube bundle reactor are manufactured from the same steel type. In many cases, the reactor hoods are manufactured from ferritic steel and plated on their inner side with stainless steel. In some cases, the reactor jacket is also manufactured from a different steel type from the remaining part of the tube bundle reactor, since rolled steel can be used for its production.

In this document, the reaction tube surrounding space is defined as the space delimited by the exterior of the reaction tubes, the two tube plates and the reactor jackets together, within which the at least one (generally liquid) heat exchange medium is conducted. In the simplest manner, in the reaction tube surrounding space, only one (preferably liquid) heat exchange medium is conducted (such a procedure is also referred to as a one-zone method in the one-zone tube bundle reactor). It is typically fed to the reaction tube surrounding space at its upper or at its lower end with its entrance temperature $T_H^{in}$ through orifices in the reactor jacket, and conducted back out of the reaction tube surrounding space at the opposite end with an exit temperature of $T_H^{out}$ through orifices in the reactor jacket.

As a result of the exothermicity of the gas phase partial oxidations, during the performance of a heterogeneously catalyzed partial gas phase oxidation, $T_H^{out} \geq T_H^{in}$ (equality relates to the case of evaporative cooling). With the aid of a heat exchanger, heat is typically withdrawn from a portion or the entirety of the (preferably liquid) heat exchange medium conducted out of the reaction tube surrounding space before it is fed back to the reaction tube surrounding space with the temperature $T_H^{in}$.

In the reaction tube surrounding space, the (preferably liquid) heat exchange medium can in principle be conducted around the reaction tubes in simple co- or countercurrent to the reaction gas mixture flowing within the reaction tubes. However, it can also be conducted around the reaction tubes in a meandering manner with the aid of corresponding deflecting plates, such that only over the entire reaction tube surrounding space does a cocurrent or countercurrent to the flow direction of the reaction gas mixture in the reaction tubes exist. When the heat exchange medium used is liquid under the use conditions, it should, appropriately from an application point of view, have a melting point in the range from 0 (or from 50) to 250° C., preferably from 120 to 200° C.

Useful such liquid heat exchange media include, for example, melts of salts such as potassium nitrate, potassium nitrite, sodium nitrite and/or sodium nitrate, and also melts of metals such as potassium, sodium, mercury and alloys of different metals. However, it is also possible to use ionic liquids (in which at least one of the oppositely charged ions comprises at least one carbon atom) or heat carrier oils (e.g. high-boiling organic solvents such as mixtures of Diphyl® and dimethyl phthalate). Useful gaseous heat exchange media include, for example, steam under elevated pressure or else flue gases. Evaporative cooling can, for example, also be undertaken with boiling water under pressure.

To improve the selectivity of target product formation, the heterogeneously catalyzed partial gas phase oxidation of an organic compound can also be performed as a multizone method (for example two-zone method) in a multizone tube bundle reactor (for example in a two-zone tube bundle reactor). In this case, within the reaction tube surrounding space, (for example two), essentially spatially separate (preferably liquid) heat exchange media (which are normally of the same type) are conducted (these may, for example, be separated by separating tube plates which have corresponding passage orifices for the reaction tubes and are inserted into the reaction tube surrounding space).

The reaction tube longitudinal section over which the particular (preferably liquid) heat exchange medium extends represents a temperature zone or reaction zone (the one-zone tube bundle reactor correspondingly has only one reaction zone).

Within the particular temperature zone, the (preferably liquid) heat exchange medium can be conducted as in the one-zone method (also relative to the flow direction of the reaction gas mixture). For the difference between $T_H^{out}$ and $T_H^{in}$, the statements regarding the one-zone method apply in an essentially identical manner to the individual temperature zone.

A graphic distinction between a one-zone method and a two-zone method (between a one-zone tube bundle reactor and a two-zone tube bundle reactor) is shown schematically, for example, by the figures of DE 102007019597.6 and the figures of EP-A 1695954. Aside from these, multizone methods are described, for example, in documents EP-A 1734030, DE-A 10313214, DE-A 10313219, DE-A 10313211, DE-A 10313208 and in the prior art cited in these documents. They are advantageous in particular when a high loading of the fixed catalyst bed with the organic compound to be oxidized partially is selected. The loading of the fixed catalyst bed with reaction gas mixture or with one reaction gas mixture component is understood to mean the amount of reaction gas mixture or reaction gas mixture component in standard liters (l (STP); the volume that the corresponding amount would theoretically take up in gaseous form at 0° C. and 1 atm) which is conducted through one liter of fixed catalyst bed per hour (pure inert beds are not included).

The temperature $T_H^{in}$ of the at least one (preferably liquid) heat exchange medium in heterogeneously catalyzed partial gas phase oxidations of organic starting compounds is typically in the range from 200 to 500° C., frequently in the range from 250 to 400° C. and in many cases in the range from 250 to 310° C.

The working pressure in a heterogeneously catalyzed partial gas phase oxidation may be either below standard pressure (for example up to 0.5 bar; the reaction gas mixture is sucked through) or above standard pressure. Typically, the aforementioned working pressure will be at values of from 1 to 5 bar, frequently from 1.5 to 3.5 bar (in each case absolute). Normally, the working pressure in a heterogeneously catalyzed partial gas phase oxidation of an organic starting compound will not exceed 100 bar.

The reaction gas input mixture (or else reaction gas entry mixture) itself may, in the different procedures in the tube bundle reactor, be conducted either from the top downward or from the bottom upward in the reaction tubes (i.e. the at least one feed orifice may be disposed either in the upper reactor hood or in the lower reactor hood). The same applies to the conduction of the (preferably liquid) heat exchange medium.

The reaction gas input mixture may, on entry into the reaction tubes, in principle be preheated to the temperature of the heat exchange medium flowing on the corresponding tube plate underside.

The temperature of the reaction gas entry mixture, on entry into the reaction tubes, may, though, also be below this temperature of the heat exchange medium. This is advisable when the reaction tubes, in flow direction of the reaction gas mixture, are charged first with a longitudinal section of shaped bodies inert to the partial oxidation, before the catalytically active section of the fixed catalyst bed comprising shaped bodies having catalytically active composition begins. In the course of flow through this inert section, the reaction gas entry mixture may then be heated to the temperature of the heat exchange medium which flows around the corresponding catalytically active reaction tube section. In principle, the reaction gas entry mixture (the product gas mixture) can also be fed in (removed) via more than one feed orifice (removal orifice) present in the corresponding reactor hood. In general, though, both the feed of the reaction gas entry mixture and the removal of the product gas mixture are each effected via only one orifice in the corresponding reactor hood.

Frequently, a heterogeneously catalyzed partial gas phase oxidation of an organic compound can, in spatial terms, be connected immediately downstream of a heterogeneously catalyzed partial gas phase oxidation of another organic compound (in this case, the target product of the preceding partial oxidation is normally the organic compounds to be oxidized partially in the downstream partial oxidation) or connected upstream of it. In particular, in these cases, the feeding or removing reactor hood can be reduced to a cylindrical tube orifice (designed as a cylindrical tube opening), which may, for example, form a cylindrical transition to an aftercooler (cf., for example, DE-A 10 2004 018267 and DE 102007019597.6).

It will be appreciated that it is also possible to perform two heterogeneously catalyzed partial gas phase oxidations which are two successive gas phase partial oxidation steps in immediate succession in the reaction tubes of a multizone tube bundle reactor (for example in a two-zone tube bundle reactor), in which case the charge of the fixed catalyst bed in the reaction tubes of the multizone tube bundle reactor normally changes in a corresponding manner at the transition from one reaction step to the next reaction step (cf., for example, the performance of multistage heterogeneously catalyzed partial gas phase oxidations in the so-called "single reactor" according to EP-A 1388533, U.S. Pat. No. 6,069,271, EP-A 990636, US-A 2006/0161019 and EP-A 1106598). Examples of the performance of such multistage heterogeneously catalyzed partial gas phase oxidations in the multizone tube bundle reactor (for example two-zone tube bundle reactor) are the heterogeneously catalyzed partial gas phase oxidation of propylene to acrylic acid and of isobutene to methacrylic acid.

In addition to molecular oxygen and the organic starting compounds to be oxidized partially as reactants, the reaction gas input mixture of a heterogeneously catalyzed partial gas phase oxidation generally also comprises a diluent gas which behaves essentially inertly under the conditions of the heterogeneously catalyzed gas phase partial oxidation. In this document, this is understood to mean those diluent gases whose constituents, present in the reaction gas mixture, under the conditions of the heterogeneously catalyzed partial gas phase oxidation—each constituent taken alone—remain unchanged to an extent of more than 95 mol %, preferably to an extent of more than 99 mol %. They have the task firstly of absorbing some of the heat of reaction and conducting it out of the tube bundle reactor as a constituent of the product gas mixture, and secondly of ensuring that the reaction gas mixture is generally outside the explosion range. Inert diluent gases typically suitable for heterogeneously catalyzed partial gas phase oxidations of organic starting compounds are, for example, $N_2$, $CO_2$, steam, noble gases and in many cases also saturated hydrocarbons (for example in a partial oxidation of unsaturated organic compounds) or mixtures of all or of some of the aforementioned possible inert diluent gases.

The reactants present in the reaction gas mixture of a heterogeneously catalyzed partial gas phase oxidation ($O_2$ and the organic starting compound) are converted as the reaction gas mixture passes through the fixed catalyst bed disposed in the reaction tubes during the residence time of the reactants over the catalyst surface.

The reaction tubes in the tube bundle reactor are, as already mentioned, generally manufactured from ferritic steel or from stainless steel and frequently have a wall thickness of a few mm, for example from 1 to 3 mm. Their internal diameter is usually a few cm, for example from 10 to 50 mm, frequently from 15 to 30 mm, or from 20 to 30 mm. The tube length extends normally to a few meters (a typical reaction tube length is in the range from 1 to 10 m, frequently from 2 to 8 m or from 2 to 6 m, in many cases from 2 to 4 m).

Appropriately from an application point of view, the number of reaction tubes accommodated in the tube bundle reactor is at least 1000, frequently at least 3000 or 5000 and in many cases at least 10 000. Frequently, the number of reaction tubes accommodated in the tube bundle reactor is from 15 000 to 30 000, or to 40 000, or to 50 000. Tube bundle reactors having a number of reaction tubes above 50 000 are usually the exception. Within the reaction tube surrounding space, the reaction tubes are normally arranged in essentially homogeneous distribution, the distribution appropriately being selected such that the distance of the central internal axes of mutually adjacent reaction tubes (the so-called reaction tube pitch) is from 25 to 55 mm, frequently from 35 to 55 mm.

Especially in the case of tube bundle reactors with a relatively large cross section of their tube plates, it is appropriate from an application point of view to leave a region without tubes in the center of the tube bundle reactor, and instead to support the upper tube plate within this region.

In principle, the total number of reaction tubes is distinguished into working tubes (the overwhelming majority of the reaction tubes) and into thermal tubes. While the working tubes are those reaction tubes in which the heterogeneously catalyzed partial gas phase oxidation in the actual sense is performed, thermal tubes primarily serve the purpose of monitoring and controlling the reaction temperature as a representative of the other reaction tubes (the working tubes). For this purpose, the thermal tubes, in addition to the fixed catalyst bed, normally comprise a thermowell which is conducted along the center of the thermal tube and is charged merely with a temperature sensor (for example a multithermoelement or an axially movable single thermoelement) (this is in many cases, but not necessarily, compensated for by an elevated internal diameter of the thermal tubes compared to the working tubes). In general, the number of thermal tubes in a tube bundle reactor is very much smaller than the number of working tubes. Normally, the number of thermal tubes is $\leq 20$. In this context, it is of particular significance that the thermal tubes are charged with fixed catalyst bed such that the profile of the reaction temperature along the interior of a thermal tube corresponds very accurately to the profile of the reaction temperature along the interior of a working tube (cf. EP-A 873 783 and EP-A 1270 065).

The profile of the reaction temperature in the reaction tubes is determined firstly by the evolution of heat caused by the exothermicity of a heterogeneously catalyzed partial gas phase oxidation and secondly, inter alia, by the transfer of this heat of reaction to the at least one heat exchange medium conducted within the reaction tube surrounding space.

Since heterogeneously catalyzed partial gas phase oxidations are typically markedly exothermic reactions, and the heat of reaction is transferred to the at least one heat exchange medium at a finite rate, the temperature of the reaction gas mixture in the course of reactive passage thereof through the fixed catalyst bed is normally different from the temperature of the fluid heat exchange medium which flows around the fixed catalyst bed outside the reaction tubes. It is typically above the entrance temperature of the heat exchange medium $T_H^{in}$ into the corresponding reaction zone (temperature zone) and, along a reaction zone, generally passes through an absolute maximum (hotspot maximum) or falls proceeding from an absolute maximum value (if appropriate via further relative maxima). These maximum values of the reaction temperature (of the temperature of the reaction gas mixture) are typically referred to as so-called "hotspot temperatures".

The hotspot temperature is therefore of particular significance because, where the reaction temperature in the reaction tube is elevated (the temperature of the fixed catalyst bed corresponds essentially to the temperature of the reaction gas mixture at the particular point), the irreversible aging processes in the fixed catalyst bed also proceed at an increased rate and cause accelerated deactivation of the fixed catalyst bed.

In this regard, it is known from the prior art that heterogeneously catalyzed partial gas phase oxidations in the reaction tubes of a tube bundle reactor which have been charged with a fixed catalyst bed can be performed over comparatively long periods (up to several years) in the case of careful operation without the fixed catalyst bed in the reaction tubes having to be renewed (freshly charged) (cf., for example, DE-A 10 350 822, DE-A 10 2004 025 445, EP-A 17 34 030 and the prior art acknowledged in these documents). The irreversible deactivation of the fixed catalyst bed is counteracted under otherwise essentially unchanged operating conditions typically by an increase in $T_H^{in}$ and/or an increase in the working pressure in the reaction tubes (cf., for example, EP-A 11 06 598, DE-A 10 351 269, EP-A 17 34 030, EP-A 990 636, DE-A 10 2004 025 445). These measures allow the target product space-time yield to be retained over prolonged operating times. However, they cause the aging process of the fixed catalyst bed to be accelerated further to an increasing extent (particular aging processes within the catalysts which contribute to aging proceed, for example, more rapidly). On attainment of a maximum value of $T_H^{in}$, the fixed catalyst bed finally has to be exchanged completely (cf. also DE-A 10 232 748, EP-A 11 06 598 and DE-A 10 2007 010 422).

However, a disadvantage of such a complete exchange is that it is comparatively complicated. The process for target product preparation has to be interrupted for a prolonged period and the costs of catalyst preparation are likewise considerable.

What are likewise desired are therefore procedures which are helpful in as far as possible prolonging the lifetime of the fixed catalyst bed in the tube bundle reactor.

As already mentioned, the above is possible to a certain extent in the case of careful operation. Careful operation is understood in the prior art to mean operating the tube bundle reactor, within the context of what is possible, overall, such that, within the individual reaction tubes, as far as possible, a uniform reaction behavior and hence also a very uniform profile of the reaction temperature (of the temperature of the reaction mixture and of the temperature of the fixed catalyst bed) is present along the individual reaction tubes.

EP-A 14 71 046, DE-A 20 2006 014 116 U1 and WO 03/059857 recommend, in this regard, performing the heterogeneously catalyzed partial gas phase oxidation of an organic starting compound in tube bundle reactors whose reaction tubes are of very uniform construction.

According to the teaching of JP-A 2006-142288, the reaction tube inner surface should additionally have a very low surface roughness in order to ensure very uniform charging of the reaction tubes with fixed catalyst bed.

Such a very uniform charging of the reaction tubes with the same fixed catalyst bed is also recommended by the documents U.S. Pat. No. 4,701,101, EP-A 14 66 883, WO 03/057653, US-A 2006/245992, US-A 2002/136678, WO 2005/051532, WO 03/076373 and JP-A 2004/195279.

At the same time, it is quite generally attempted in heterogeneously catalyzed gas phase reactions to minimize the energy demand required for the conveying of the reaction gas. As a measure for achieving this objective, preference is given to using annular shaped catalyst bodies for the configuration of the fixed catalyst bed, since they cause a particularly low pressure drop in the course of passage of the reaction gas through the fixed catalyst bed (cf., for example, WO 2005/03039). A further advantage of annular shaped catalyst bodies normally consists in reduced diffusion pathways and, resulting from this in many cases, in an improved target product yield.

In the simplest case, such an annular shaped catalyst body consists only of catalytically active composition which may, if appropriate, be diluted with inert material (which is, for example, in many cases incorporated for reinforcement reasons) (if appropriate, shaping assistant is also present; for example graphite). Such annular geometric shaped catalyst bodies are typically referred to as annular unsupported catalysts.

However, a disadvantage of annular unsupported catalysts is their generally not fully satisfactory mechanical stability in the course of filling into the reaction tubes. Although this can be improved by an increase in their wall thickness, a disadvantage of relatively large wall thicknesses is that they are accompanied by a lengthening of the diffusion pathway out of the reaction zone, which promotes undesired subsequent reactions and hence reduces the target product selectivity.

A resolution of the contradiction which exists in the case of unsupported catalyst rings between required mechanical stability (increasing wall strength) on the one hand and limiting of the diffusion pathway out of the reaction zone (decreasing wall strength) on the other hand, while maintaining the otherwise particularly advantageous ring geometry, is opened up by annular coated catalysts. These are annular shaped catalyst bodies which consist of an annular (mechanically particularly stable) (catalytically inactive) shaped support body which is generally inert with regard to the gas phase partial oxidation and a catalytically active composition (active composition) applied to its surface.

It can be prepared, for example, by coating the annular shaped support bodies (generally consisting of catalytically inactive (frequently oxidic (e.g. hard-fired)) material; consisting of inert material) with finely divided active composition using a generally liquid binder. Alternatively (or in a mixture with finely divided precursor composition), the shaped support bodies may also be coated with a finely divided precursor composition of the active composition using a generally liquid binder, and the conversion to the active annular shaped catalyst bodies can be effected by subsequent (for example oxidative and/or reductive) thermal treatment (if appropriate in an atmosphere comprising molecular oxygen). The coating can be effected in the simplest manner, for example, by moistening the surface of an inert annular shaped support body (or else simply just "support body") by means of a liquid binder and then adhering finely divided (pulverulent) active composition or finely divided (pulverulent) precursor composition on the moistened surface. Subsequently, normally at least a portion of the liquid binder (generally under the action of heat) is volatilized before the annular coated catalysts are ready to charge a reaction tube (a further thermal treatment can be effected, for example, within the reaction tubes (for example for the purpose of removing residual binder [cf., for example, DE-A 102005010645])). Alternatively, the annular shaped support bodies can also be sprayed with a suspension of finely divided active composition and/or finely divided precursor composition.

Instead of coating the generally inert annular shaped support body with finely divided active composition or with finely divided precursor composition, the annular shaped support body can in many cases also be impregnated with a solution (a molecular and/or colloidal solution) of the catalytically active substance or with a solution of a precursor substance and then the solvent can be volatilized and, if appropriate, a chemical reduction and/or thermal treatment (if appropriate in a molecular oxygen-comprising atmosphere) can follow. The annular shaped catalyst bodies which result in this way are frequently also referred to as supported or impregnated catalysts in the literature. However, they will likewise be encompassed in this document under the generic term "coated catalysts".

Descriptions of processes for preparing annular coated catalysts which are suitable as catalysts for heterogeneously catalyzed partial gas phase oxidations can be found, for example, in the documents DE-A 290 9671, EP-A 714 700, German application 102007017080.9, WO 2004/108267, DE 10 2005 010 645 A1, DE-A 103 13 209, DE-A 103 25 488, DE-A 103 60 058, DE-A 103 51 269, DE-A 103 50 822, WO 2007/009922, DE-A 100 49 873, German application 102007010422.9, DE-A 40 06 935, DE-A 198 23 275, DE-A 198 39 001, DE-A 198 23 262, DE-A 103 44 844, US 2006/0205978 and EP-A 758 562, and the prior art acknowledged in these documents.

An unwanted by-product, which, though, generally cannot be avoided completely, in the preparation of annular coated catalysts is the formation of adhering pairs of annular coated catalysts. These are two coated catalyst rings which adhere firmly to one another. Their formation is attributable ultimately to the fact that the normally liquid binder typically used to apply the active composition coating to the annular support body in the preparation of coated catalysts is capable of bringing about not only the bonding of active composition and shaped support body but, to a limited degree, also the unwanted bonding of two annular coated catalysts. Essentially, the formation of such adhering pairs is restricted to two types: a) fused adhering pairs and b) tandem adhering pairs.

In the fused adhering pairs, two annular coated catalysts (an annular coated catalyst has the geometry E×I×H (external diameter×internal diameter×height)) adhere to one another by their cylindrical shells (outer walls) essentially over the entire height H. They essentially adhere to one another resting alongside one another at the same height (their outer surfaces adhere to one another).

In the tandem adhering pairs, two annular coated catalysts adhere to one another by their annular cross-sectional areas which delimit the particular coated catalyst ring at the top and at the bottom. The upper ring surface of one coated catalyst ring adheres on the lower ring surface of one coated catalyst ring adheres (sticks) on the lower ring surface of the other coated catalyst ring. In this way, what is effectively formed is a coated catalyst super-ring which has the same external diameter E and the same internal diameter I as the two coated catalyst rings which constitute it, but whose height is 2 H.

While the formation of tandem adhering pairs in the preparation of annular coated catalysts is essentially unavoidable, fused adhering pairs form in the preparation of annular coated catalysts essentially (in particular) when H is at least >0.5 E.

Overall, the total amount M of adhering pairs of coated catalyst rings formed in the preparation of one production charge of annular coated catalysts, based on the total weight of the production charge, is $\leq 5\%$ by weight. Usually, M, on the same basis, is even $\leq 4$, or $\leq 3$, or $\leq 2$, or $\leq 1\%$ by weight. In the case of careful preparation of annular coated catalysts, M, on the same basis, may even be $\leq 0.8\%$ by weight, or $\leq 0.5\%$ by weight, or $\leq 0.3\%$ by weight, $\leq 0.2\%$ by weight, or $\leq 0.1\%$ by weight. In general, M is, however, on the same basis, >0, usually $\geq 0.005$ and frequently even $\geq 0.01\%$ by weight.

Owing to the aforementioned comparatively low amounts of adhering pairs of coated catalyst rings formed, no increased significance was attributed to their presence in the use of production charges of annular coated catalysts for the configuration of the fixed catalyst bed in the reaction tubes of tube bundle reactors.

However, extremely careful investigations by the applicant with regard to the configuration of fixed catalyst beds in reaction tubes of tube bundle reactors using annular coated catalysts have led to the result that, in the case of an unfavorable position of an adhering pair of coated catalyst rings in the fixed catalyst bed disposed in a reaction tube of a tube bundle reactor, the hotspot temperature in this reaction tube can be increased perceptibly merely by the presence of a single adhering pair of coated catalyst rings in the fixed catalyst bed.

However, an elevated hotspot temperature means accelerated aging of the corresponding fixed catalyst bed charge of a reaction tube. In order to compensate at least temporarily for such an accelerated aging process with regard to the desired space-time yield of target product in a heterogeneously catalyzed partial gas phase oxidation performed in a tube bundle reactor, an accelerated increase of $T_H^{in}$ of the at least one heat exchange medium is required, which in turn causes an additional acceleration of the aforementioned aging process. The ultimate overall effect which results is a reduced lifetime of the fixed catalyst bed charge of the tube bundle reactor, which is undesired for the reasons already described.

The presence of one (or else more) adhering pair(s) of coated catalyst rings is particularly disadvantageous in the fixed catalyst bed of a thermal tube. The profile of the reaction temperature within the thermal tubes arranged in the tube bundle reactor to be representative of all working tubes forms, as already stated, the basis for the control of the overall operation of a tube bundle reactor (for example the control of the loading of the fixed catalyst bed with reaction gas, the control of the composition of the reaction gas mixture, the setting of the particular $T_H^{in}$ etc).

In general, the control of the overall operation, for safety reasons, is directed to those thermal tubes whose operating data are the most marginal. When these operating data are representative of the operating data of the corresponding working tubes only to a limited degree owing to the presence of adhering pairs of coated catalyst rings in the fixed catalyst bed of the corresponding thermal tubes, this normally leads to the effect that the overall tube bundle reactor is not operated in its optimal operating state.

BRIEF SUMMARY OF THE INVENTION

Against this background, it was an object of the present invention to provide an improved process for charging the reaction tubes of a tube bundle reactor with a fixed catalyst bed which is suitable for performing a heterogeneously catalyzed partial gas phase oxidation of an organic starting compound and which is configured using annular coated catalysts, said process having the disadvantages of the prior art processes described in reduced form at worst.

DETAILED DESCRIPTION OF THE INVENTION

Figure 1:
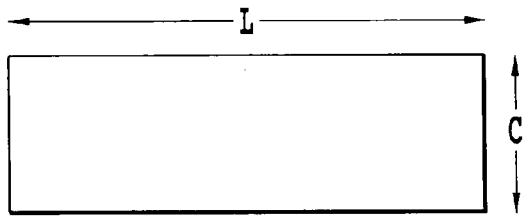
FIG. 1 illustrates the geometric form of the screen orifice(s) being a rectangle.

Accordingly, a process has been found for introducing a portion withdrawn from at least one production charge of annular coated catalysts K into a reaction tube of a tube bundle reactor for the purpose of charging this reaction tube with a fixed catalyst bed suitable for performing a heterogeneously catalyzed partial gas phase oxidation of an organic starting compound, which comprises, before the withdrawal of the portion from the at least one production charge and/or after the withdrawal or before the introduction of the portion withdrawn into the reaction tube, removing adhering pairs of annular coated catalysts K formed in the preparation of the at least one production charge of annular coated catalysts K at least partly from the at least one production charge and/or from the portion withdrawn.

Advantageously in accordance with the invention, before the withdrawal of the portion from the at least one production charge of annular coated catalysts K, adhering pairs of coated catalysts K formed in the course of preparation thereof, based on the total content (on the total amount) of adhering pairs of coated catalyst rings which are present as a result of the preparation in the at least one production charge, are removed from the at least one production charge to an extent of at least 20% by weight, preferably to an extent of at least 30% by weight, more preferably to an extent of at least 40% by weight and most preferably to an extent of at least 50% by weight. It is even better when, in the process according to the invention, before the withdrawal of the portion from the at least one production charge of annular coated catalysts K, adhering pairs of coated catalysts K formed in the preparation thereof, based on the total content (on the total amount) of adhering pairs of coated catalyst rings present as a result of the preparation in the at least one production charge, are removed to an extent of at least 60% by weight, or to an extent of at least 70% by weight, preferably to an extent of at least 80% by weight or an extent of at least 90% by weight, more preferably to an extent of at least 95% by weight or to an extent of at least 98% by weight and most preferably to an extent of 100% by weight.

It will be appreciated that it is also possible in accordance with the invention only after (or additionally after) the withdrawal of the portion from the at least one production charge of annular coated catalysts K to withdraw (remove) adhering pairs of coated catalyst rings present as a result of preparation in this withdrawn portion, based on their total amount present in the portion withdrawn, to an extent of at least 20% by weight, or to an extent of at least 30% by weight, or to an extent of at least 40% by weight or to an extent of at least 50% by weight, or to an extent of at least 60% by weight, or to an extent of at least 70% by weight, or to an extent of at least 80% by weight, or to an extent of at least 90% by weight, or to an extent of at least 95% by weight and most preferably to an extent of 100% by weight, before this portion is introduced into the reaction tube.

In principle, in heterogeneously catalyzed partial gas phase oxidations, the fixed catalyst bed in each individual reaction tube may consist only of the portion, essentially of equal size, withdrawn in each case from the at least one production charge of annular coated catalysts K.

It will be appreciated that the fixed catalyst bed, over the total length of a reaction tube may, though, also consist of a homogenized mixture of a plurality of (i.e. at least two) mutually distinguishable types $S^i$ of geometric shaped catalyst bodies or of geometric shaped catalyst bodies and geometric shaped inert bodies (i.e. such a mixture may consist of at least two mutually distinguishable types of geometric shaped catalyst bodies, or of a single type of geometric shaped catalyst bodies and of a single type of geometric shaped inert bodies, or of at least two types of mutually distinguishable geometric shaped catalyst bodies and a single type of geometric shaped inert bodies, or of at least two types of mutually distinguishable geometric shaped catalyst bodies and at least two types of mutually distinguishable geometric shaped inert bodies).

Among these mutually different types $S^i$, it is possible, if appropriate, for only one type of annular coated catalysts K relevant in accordance with the invention to be present. Possible distinguishing features of the mutually different types $S^i$ are the type of geometry, the type of active composition, the type of the support material, etc.

In principle, useful materials for the geometric shaped inert bodies (they serve the purpose of diluting geometric shaped catalyst bodies in a fixed catalyst bed and in this way of restricting the local evolution of heat in the fixed catalyst bed disposed in the reaction tube as the reaction gas mixture flows through it) are the same materials which can also be used for the inert (for example annular) shaped support bodies for preparing coated catalysts and essentially do not intervene in the course of the gas phase partial oxidation.

The latter means here generally that, when the reaction gas mixture, under the same reaction conditions, is conducted through a reaction tube charged only with inert shaped support bodies (inert shaped diluent bodies), the conversion of the organic starting compound to be oxidized partially is $\leq 5$ mol %, usually $\leq 2$ mol %.

Useful such inert materials for geometric shaped support bodies or inert shaped diluent bodies for numerous heterogeneously catalyzed partial gas phase oxidations are, for example, porous or nonporous aluminum oxides, silicon dioxide (or silicon oxide in general), thorium dioxide, zirconium oxide, silicon carbide or silicates such as magnesium silicate or aluminum silicate (e.g. C 220 steatite from CeramTec), but also metals, for example stainless steel or aluminum (cf., for example, US 2006/0205978).

In principle, all inert shaped support bodies are also useful as geometric shaped inert bodies for diluting geometric shaped catalyst bodies in a fixed catalyst bed.

Such a dilution allows the volume-specific activity of a fixed catalyst bed, as already stated, to be adjusted specifically to the requirement of the particular heterogeneously catalyzed partial gas phase oxidation.

Geometric shaped inert bodies and geometric shaped catalyst bodies in a homogenized mixture corresponding to the above preferably have the same geometry or at least a similar geometry.

The wording "homogenized mixture" means that measures have been taken in order to mix the mutually different types of geometric shaped bodies (or the different longest dimensions within one type) homogeneously with one another. Ideally, the homogeneous mixing along the entire longitudinal section reaches the statistical average, also in relation to the particular individual type.

In many cases, a reaction tube charge (a reaction tube filling) with one fixed catalyst bed, though, also consists of a plurality of mutually distinguishable longitudinal sections installed one on top of another (in succession) (fixed catalyst bed (longitudinal) sections, catalyst bed sections). In this case, each individual longitudinal section may be configured uniformly over its length as has already been detailed for a reaction tube charged uniformly over its total reaction tube length. At the transition from one intrinsically homogeneous bed section to the next intrinsically homogenous bed section, the configuration (composition) of the bed normally changes abruptly. Along an individual reaction tube, this gives rise to fixed catalyst bed sections which have a heterogeneous structure. This is also referred to as a structured filling (or charge) of the reaction tubes.

At the start (viewed in flow direction of the reaction gas flowing through the reaction tube) and/or at the end of the reaction tube, the fixed catalyst bed is frequently concluded by a sole bed of geometric shaped inert bodies. Such sole inert beds are typically not included in the fixed catalyst bed.

Appropriately from an application point of view, in the case of a structured filling of the reaction tubes, the contents of an intrinsically homogeneous bed section, following the teaching of DE-A 10 2004 023249, will be obtained beforehand in homogenized form and be packaged as such a bed section portion. When annular coated catalysts K are constituents of such a bed section portion packaged beforehand, they are introduced in accordance with the invention into the reaction tube as part of the corresponding bed section portion. In other words, for the advance preparation of the bed section portion, the at least one production charge of annular coated catalysts K (preferably in accordance with the invention), once adhering pairs of coated catalyst rings which have formed in the course of its preparation and are present therein as a result have been removed at least partly from it in the inventive manner, the required portion is withdrawn and homogenized with the other geometric shaped bodies of the bed section portion, the resulting homogenized mixture of geometric shaped bodies is introduced into the packaging and the packing thus obtained, in the course of the charging of the reaction tubes with the desired fixed catalyst bed, is emptied into the reaction tube. In other words, the inventive introduction of a portion withdrawn from at least one production charge of annular coated catalysts K into a reaction tube of a tube bundle reactor need not necessarily be effected separately, but can also be effected in a homogenized mixture with other geometric shaped bodies (it will be appreciated that the adhering bodies can also be removed only after the withdrawal of a portion from the at least one production charge).

In general, the filling of a reaction tube with a structured fixed catalyst bed is configured such that the volume-specific activity of the fixed catalyst bed increases in flow direction of the fixed catalyst bed.

This can be realized, for example, in a simple manner by virtue of the fixed catalyst bed consisting of mutually different longitudinal sections which differ from one another merely in that one type of annular coated catalysts K is diluted with different proportions of only one type of shaped inert bodies. In flow direction of the reaction gas, the degree of dilution with shaped inert bodies decreases, and the last longitudinal section of the fixed catalyst bed in flow direction will frequently consist only of annular coated catalysts K.

A volume-specific activity of the fixed catalyst bed increasing in flow direction of the reaction gas can, however, also be realized by virtue of the individual longitudinal sections of the fixed catalyst bed consisting in each case only of one type of annular coated catalyst, the ring geometries of the mutually different coated catalysts typically being essentially the same, but the active compositions differ from one another on the basis of a different elemental composition, with the proviso that the catalytic activity of the active composition used in each case increases in flow direction of the reaction gas mixture. The volume-specific activity of an intrinsically homogeneous longitudinal section of a fixed catalyst bed charge of a reaction tube is normally increased when, with continuous charging of the reaction tube as in the corresponding longitudinal section of the reaction tube under otherwise identical reaction conditions (i.e. identical composition of the reaction gas mixture, identical loading of the fixed catalyst bed charge with reaction gas mixture and identical entrance temperature of the heat carrier and identical flow conditions of the heat carrier), an increased conversion of the organic starting compound to be oxidized partially results.

Examples of structured fillings of reaction tubes for the purpose of performing heterogeneously catalyzed partial gas phase oxidations with volume-specific activity increasing in flow direction of the reaction gas mixture using annular coated catalysts are disclosed, for example, by the documents EP-A 173 4030, DE-A 19823262, DE-A 19823275, German application 102007010422.9, EP-A 1734030 and German application 102007019597.6.

The process according to the invention is of particular relevance when the fixed catalyst bed introduced into the reaction tubes consists of annular coated catalysts to an extent of at least 20%, or to an extent of at least 30%, or to an extent of at least 40%, or to an extent of at least 50%, or to an extent of at least 60%, or to an extent of at least 70%, or to an extent of at least 80%, or to an extent of at least 90%, or to an extent of at least 95%, or to an extent of 100% of its weight.

Preferably in accordance with the invention, at least 20% by weight, preferably at least 40% by weight, more preferably at least 60% by weight, even more preferably at least 80% by weight and at best the entirety of the annular coated catalysts present in a reaction tube are introduced into the reaction tube by the inventive procedure.

Advantageously in accordance with the invention, the annular coated catalysts introduced into the reaction tube by the inventive procedure are especially those of a fixed catalyst bed disposed in a reaction tube which, viewed in flow direction of the reaction gas mixture, are disposed in the first 80%, or in the first 60%, or in the first 40%, or in the first 20% of the total fixed catalyst bed (charge) length.

In principle, all statements made in this document with regard to heterogeneously catalyzed partial gas phase oxidations of organic starting compounds and their performance in a fixed catalyst bed disposed in the reaction tubes of a tube bundle reactor apply in particular when the reaction tubes have been charged with the fixed catalyst bed in the inventive manner.

The steam content of the reaction gas input mixture in these heterogeneously catalyzed partial gas phase oxidations may in principle be 0 (vanishing).

Normally, the steam content of the reaction gas input mixture in these heterogeneously catalyzed partial gas phase oxidations will normally, however, be >0% by volume. Frequently, the steam content of the reaction gas input mixture will be from $\geq 0.1$ to 60% by volume, or from $\geq 0.2$ to 50% by volume or from $\geq 2$ 0.3 to 40% by volume, or from $\geq 0.4$ to 30% by volume, or from $\geq 0.5$ to 25% by volume, or from $\geq 0.75$ to 20% by volume, or from $\geq 1$ to 15% by volume, or from $\geq 2$ to 10% by volume. Owing to its comparatively elevated specific heat capacity, steam is generally an excellent inert diluent gas for heterogeneously catalyzed partial gas phase oxidations of organic starting compounds and in many cases has a beneficial effect on the catalyst activity.

Useful sources for the molecular oxygen required in the reaction gas input mixture for a heterogeneously catalyzed partial gas phase oxidation include air, pure molecular oxygen, air depleted in molecular oxygen or other mixtures of inert gas and molecular oxygen.

The content in the reaction gas input mixture of the organic starting compound to be oxidized partially under heterogeneous catalysis may, in heterogeneously catalyzed partial gas phase oxidations for which the process according to the invention is relevant (i.e. especially all heterogeneously catalyzed partial gas phase oxidations discussed in this document), be up to 50% by volume or more.

Frequently, this content will be from $\geq 2$ to 20% by volume, or from $\geq 4$ to 12% by volume.

When the reaction gas input mixture comprises the molecular oxygen in a substoichiometric amount based on the desired partial oxidation, the excess amount present in the reaction gas input mixture of the organic starting compound to be oxidized partially may in principle function as an inert diluent gas. When the reaction gas input mixture comprises molecular oxygen in a superstoichiometric amount based on the partial oxidation, it will, appropriately in accordance with the application, be selected such that the composition of the reaction gas input mixture is outside the explosive composition range.

It will be appreciated that the composition of the reaction gas input mixture may, though, also be within the explosive composition range, as is normally the case, for example, in the case of preparation of phthalic anhydride from o-xylene and/or naphthalene.

On the grounds of a very long catalyst lifetime, the proportion of the molecular oxygen in the reaction gas input mixture of a heterogeneously catalyzed partial gas phase oxidation for which the process according to the invention is relevant will generally preferably be selected such that the product gas mixture of the gas phase partial oxidation still comprises excess molecular oxygen (for example up to 3% by volume).

The volume flow rate of the heating medium (of the at least one heat exchange medium (preferably a liquid heat exchange medium)) in the reaction tube surrounding space in gas phase partial oxidations relevant in accordance with the invention is typically such that the temperature rise (caused by the exothermicity of the partial oxidation) of the (preferably liquid) at least one heat exchange medium, from its entry point into the tube bundle reactor up to its exit point from the tube bundle reactor, is from $\geq 0$ to 15° C., or from $\geq 0$ to 10° C., frequently from $\geq 2$ to 8° C., preferably from $\geq 3$ to 6° C.

The loading of the fixed catalyst bed with the organic starting compound to be oxidized partially in a gas phase partial oxidation relevant in accordance with the invention will generally be $\geq 50$ l (STP)/l·h, usually $\geq 75$ l (STP)/l·h, in many cases $\geq 100$ l (STP)/l·h. Usually, this loading will, however, be $\leq 600$ l (STP)/l·h.

The loading of the fixed catalyst bed with reaction gas input mixture in a gas phase partial oxidation relevant in accordance with the invention will frequently be $\geq 1500$ l (STP)/l·h, or $\geq 2000$ l (STP)/l·h, or $\geq 2500$ l (STP)/l·h, or $\geq 3000$ l (STP)/l·h, or $\geq 4000$ l (STP)/l·h. In general, the aforementioned loading in such heterogeneously catalyzed partial gas phase oxidations will, however, be at values of $\leq 6000$ l (STP)/l·h, or $\leq 5000$ l (STP)/l·h. The conversion of the organic starting compound to be oxidized partially will, in gas phase partial oxidations relevant in accordance with the invention, typically be $\geq 50$ mol %, frequently $\geq 70$ mol %, in many cases $\geq 80$ mol % and often $\geq 90$ mol % (based on single pass of the reaction gas mixture through the fixed catalyst bed). The selectivity of target product formation will typically be $\geq 70$ mol %, frequently $\geq 80$ mol % and in many cases $\geq 90$ mol %.

Otherwise, the boundary conditions of a heterogeneously catalyzed partial gas phase oxidation relevant in accordance with the invention will, appropriately in accordance with the application, overall, normally be selected such that the temperature difference between the hotspot temperature of the reaction gas mixture in the individual reaction zones (temperature zones) of the tube bundle reactor and the particular accompanying $T_H^{in}$ of the temperature zone, even in long-term operation, generally does not exceed 100° C. In partial oxidations with exothermicity which is not so pronounced, this temperature difference, even in long-term operation, will frequently be $\leq 80°$ C. or $\leq 70°$ C., and is in many cases from 20 to 70° C. or to 50° C.; this temperature difference, even in long-term operation, is preferably low.

Moreover, the aforementioned boundary conditions are typically selected such that the "peak-to-salt temperature sensitivity" (cf. definition in EP-A 1106598), especially also in long-term operation, is $\leq 9°$ C., but $\leq 7°$ C., or $\leq 5°$ C., or $\leq 3°$ C. Among other factors, this also takes account of the fact that the temperature of the at least one heat exchange medium, viewed over the cross section of the tube bundle reactor, is generally not completely homogeneous (uniform), but rather has a slight gradient.

The external diameter E of the annular shaped support bodies of coated catalysts K to be introduced into a reaction tube in accordance with the invention is typically from 4 to 10 mm, the accompanying height (length) H is from 2 to 10 mm and their wall thickness is generally from 1 to 4 mm.

The external diameter E of such annular shaped support bodies is preferably from 4 to 8 mm, the wall thickness from 1 to 2 mm and the height H from 3 to 7 mm.

Particularly frequently employed geometries of annular shaped support bodies of coated catalysts K to be introduced in accordance with the invention are the ring geometries (E (external diameter)×I (internal diameter)×H (height)) 8 mm×5 mm×6 mm, 7 mm×4 mm×7 mm, 7 mm×4 mm×4 mm and 7 mm×4 mm×3 mm.

The thickness of the active composition coating applied to the annular shaped support body is generally from 10 to 3000 or to 1000 μm, preferably from 10 to 500 μm, frequently from 100 to 500 μm and in many cases from 200 to 300 μm.

The catalytic active composition applied to the annular shaped support bodies in the case of coated catalysts K is generally at least one multielement oxide (frequently at least one metal oxide) or compositions which comprise at least one multielement oxide (for example multimetal oxide).

In principle, the term "multielement oxide" in this document means that the catalytically active oxide composition, as well as oxygen, also comprises at least two further, different elements. Particularly frequently, the catalytically active multielement oxide compositions used are those which have at least two metallic elements, especially at least two transition metal elements. In this case, reference is made to multimetal oxide compositions. In general, catalytically active multielement oxide compositions are not simple physical mixtures of oxides of their elemental constituents, but rather heterogeneous mixtures of complex poly compounds of these elements. In principle, useful catalytically active multielement oxide compositions also include, however, simple physical mixtures (for example agglomerates of finely divided element oxides) of oxides of their elemental constituents (for example in the case of the annular coated catalysts K for preparing phthalic anhydride from o-xylene and/or naphthalene), which is why the generic term "multielement oxide compositions" in this document is intended to encompass such mixtures (agglomerates).

In a multitude of cases, the at least one catalytically active multielement oxide is one which comprises
a) the elements Mo, Fe and Bi, or
b) the elements Mo and V, or
c) the element V and additionally P and/or Ti.

In addition, useful coated catalysts to be introduced into a reaction tube in accordance with the invention are those which comprise, as an active composition, elemental silver on an oxidic annular shaped support body.

A removal of adhering pairs of annular coated catalysts K formed in the preparation of the at least one production charge of annular coated catalysts K from the at least one production charge can be effected manually in the simplest manner, i.e. by manual sorting. Alternatively, the removal can also be undertaken by wind sifting, in which the different weight of coated catalysts K and their adhering pairs is exploited.

For example, the entirety or a portion of the at least one production charge can be conducted through a lock which opens only to admit a single coated catalyst ring K (the detection can be effected, for example, by means of optical methods). When the lock is subsequently blocked by an adhering pair, it is blown away by an appropriately directed gas stream (for example an air stream) (i.e. the lock entry is unblocked by blowing). Beyond the lock, annular coated catalyst K can then be withdrawn for introduction into a production tube.

Particularly advantageously from an application point of view, a removal of adhering pairs of annular coated catalysts K formed in the preparation of the at least one production charge of annular coated catalysts K will, however, be undertaken by a screening process. In this process, the screen residue which remains (also known as "oversize") is normally essentially the adhering pairs (and any other multiple annular coated catalysts K formed in the course of preparation of the annular coated catalysts K), while the material passing through the screen (also known as "undersize") typically comprises essentially the annular coated catalysts K.

When, for the annular geometry $E \times I \times H$ of the coated catalyst K (E=external diameter, I=internal diameter, H=height), the relationship $H \leq 0.5 \cdot E$ applies, the formation of fused adhering pairs of coated catalyst rings in the preparation of the annular coated catalysts K is, according to the investigations of the applicant, generally quantitatively negligible with most customary binders compared to the formation of tandem adhering pairs of coated catalyst rings.

Against this background, for the inventive removal of adhering pairs from the at least one production charge of aforementioned annular coated catalysts K (or from the portion withdrawn therefrom), an advisable process for screening is one with the aid of a screen which has screen orifices $O_1$ within whose continuous outline a rectangle R with the side lengths L and C can be inscribed with the proviso $M_1$, $$L > E \geq 2H > C > H,$$

but not with the proviso $M_1^*$, $$L > C \geq 2H.$$

Preferably, in the case of the aforementioned annular coated catalysts K, an advisable process for screening is one with the aid of a screen which has screen orifices $O_2$ within whose continuous outline a rectangle R with the side lengths L and C can be inscribed with the proviso $M_2$, $$L > E \geq 2H > 1.75H \geq C \geq 1.25H,$$

but not with the proviso $M_2^*$, $$L > C > 1.75H.$$

Both in the case of the screen orifices $O_1$ and in the case of the screen orifices $O_2$, it is favorable in accordance with the invention when $L \geq 1.05 \cdot E$, better $\geq 1.1 \cdot E$, preferably $\geq 1.25 \cdot E$, more preferably $\geq 1.5 \cdot E$ and most preferably $\geq 1.75 \cdot E$.

In principle, both in the case of the screen orifices $O_1$ and in the case of the screen orifices $O_2$, $L \geq 2$ E, or $\geq 2.5 \cdot E$. In general, L will, however, both in the case of the screen orifices $O_1$ and in the case of the screen orifices $O_2$, be $\leq 20 \cdot E$, in many cases $\leq 15 \cdot E$, frequently $\leq 10 \cdot E$ and often $\leq 5 \cdot E$. However, this length restriction is frequently caused by secondary features, for example an outstanding mechanical stability of the screen, rather than by the screening action desired.

In the case that, in the aforementioned cases, a screening removal of fused adhering pairs is additionally desired, the following conditions should be satisfied for the proviso $M_1$:

$$2E > L > E \geq 2H > C > H,$$

preferably even $$1.9E > L > E \geq 2H > C > H,$$

and the following conditions should correspond and may be satisfied for the proviso $M_2$:

$$2E > L > E \geq 2H > 1.75H \geq C \geq 1.25H,$$

and preferably even $$1.9E > L > E \geq 2H > 1.75H \geq C \geq 1.25H.$$

Appropriately from an application point of view, both the continuous outline of the screen orifices $O_1$ and the continuous outline of the screen orifices $O_2$ are a rectangle with the side lengths L and C (in simplified language, this document frequently refers to the geometric form of the continuous outline of a screen orifice as the "geometric form of the screen orifice"), as shown by FIG. 1.

Figure 2:
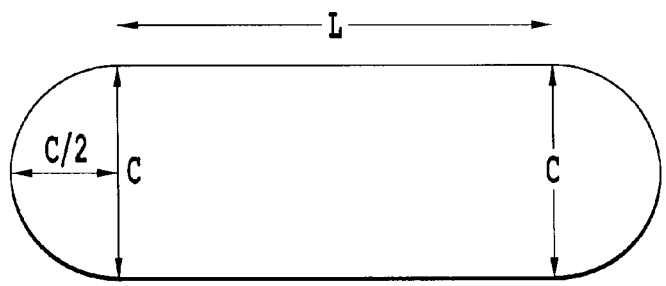
FIG. 2 illustrates the form of the screen orifice(s) being an elongated hole.

It will be appreciated that both a screen orifice $O_1$ and a screen orifice $O_2$ may, though, also be an elongated hole, as shown by way of example by FIG. 2.

Figure 3:
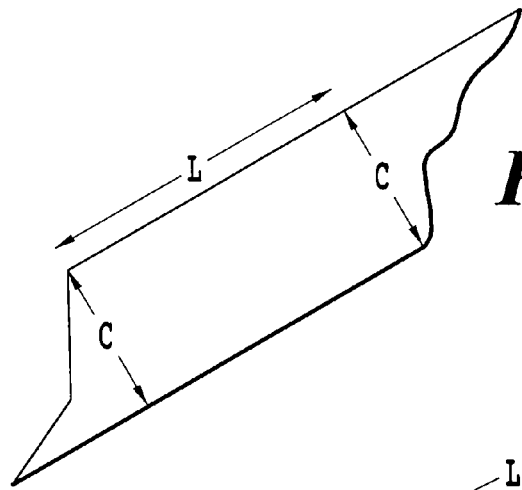
FIG. 3 illustrates the form of the screen orifice(s) being an irregular shape.
Figure 4:
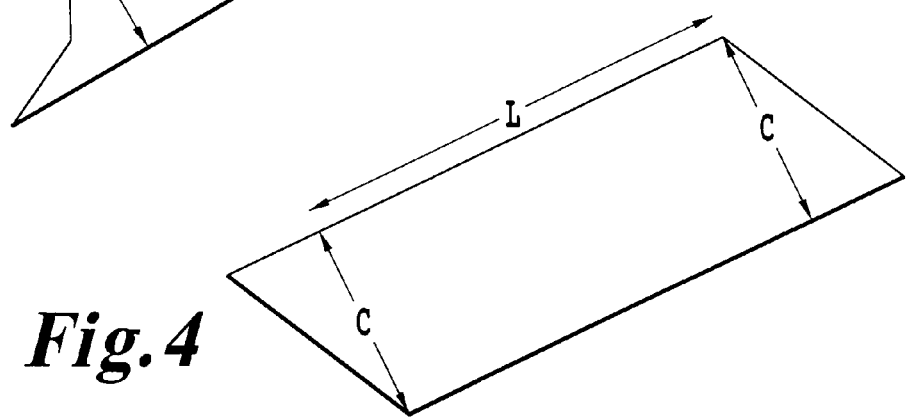
FIG. 4 illustrates the geometric form of the screen orifice(s) being a parallelogram.

The geometry of such an elongated hole derives from that of the relevant rectangle with the side lengths L and C in a simple manner by virtue of the rectangle sides with the length C each being replaced by a semicircle with the diameter C (the hole width), the semicircular curve pointing outward from the rectangular area. A comparatively general form of a possible screen orifice (or its outline) which is suitable in accordance with the invention in the sense described above is shown by way of example by FIG. 3. Of course, another possible screen orifice (or its outline (both expressions are, as already stated, used in an equivalent manner in this document)) suitable in accordance with the invention in the sense described above is a parallelogram, as shown by way of example in FIG. 4. In addition, another useful outline of a screen orifice suitable in accordance with the invention in the sense described above is one which derives from a rectangular outline by virtue of all or at least some of the corners of the rectangle having been rounded off.

When, for the annular geometry E×I×H of the annular coated catalyst K, the relationships E≧H>0.5·E apply, the formation of fused adhering pairs of coated catalyst rings in the preparation of annular coated catalysts K, according to the investigations of the applicant, becomes increasingly significant with increasing H/E ratio (depending on the binder used).

Against this background, a recommended process for the inventive removal of adhering pairs from the at least one production charge (or from the portion withdrawn therefrom) of such (aforementioned) annular coated catalysts K is a process for screening with the aid of a screen which has screen orifices $O_3$ within whose continuous outline a rectangle R with the side lengths L and C can be inscribed with the proviso $M_3$,

L>E<2H>C>H, but not with the proviso $M_3^*$,

L≧C≧2H.

In the case of the aforementioned annular coated catalysts K, a recommended process is preferably a process for screening with the aid of a screen which has screen orifices $O_4$ within whose continuous outline a rectangle R with the side lengths L and C can be inscribed with the proviso $M_4$,

2E>L>E<2H>C>H, but not with the proviso $M_4^*$,

L≧C≧2H.

More preferably, a recommended process in the case of the aforementioned annular coated catalysts K is a process for screening with the aid of a screen which has screen orifices $O_5$ within whose continuous outline a rectangle R with the side lengths L and C can be inscribed with the proviso $M_5$,

2H>L>E<2H>C>H, but not with the proviso $M_5^*$,

L≧C≧2H.

Preferably in accordance with the invention, the rectangles R to be inscribed into the screen orifices $O_3$, $O_4$ or $O_5$ are its special form of a square where L=C. The latter is found to be beneficial especially for the screen throughput.

Appropriately from an application point of view, the continuous outlines of the screen orifices $O_3$, $O_4$ and $O_5$ are also each a rectangle with the side lengths L and C (preferably its special form of a square where L=C).

It will be appreciated that a screen orifice $O_3$ or $O_4$ or $O_5$ may also be an elongated hole (which may also be derived here from a square). Of course, a parallelogram is also possible as such an outline, or a rectangle of whose corners all or at least some have been rounded off.

In principle, a screen to be used in accordance with the invention may, for example, have a plurality of different types of screen orifices possible in accordance with the invention. Advantageously in accordance with the invention, a screen used in a process according to the invention will, however, have not more than three, and generally not more than two, different types of screen orifices which satisfy the inventive profile of requirements. Very particularly advantageously, a screen to be used in accordance with the invention will, however, have only one type of inventive screen orifices.

The term "screen" is used in this document synonymously with the term "screen plate". Otherwise, the term "screen" or "screen plate" is used in this document in the sense of the definition given in EP-A 1 726 358 in column 5 lines 48 to 57.

In other words, the screen plate may, for example, be configured as a grid or grille, as a perforated or slotted sheet (i.e. as a sheet with punched, lasered, water-cut or milled screen orifices) or as a screen fabric (it consists of wires woven together, and the wires may be round or profiled).

In principle, for a screening process according to the invention, useful screen plate variants are also any other screen plate variants detailed in Aufbereitungs-Technik-No. 11/1960, p. 457 to 473 or in Chem.-Ing.-Techn. 56 (1984) No. 12, page 897 to 907. It will be appreciated that it is also possible to use, for a screening process according to the invention, all screen plates detailed in "Sieben und Siebmaschinen, Wiley-VCH GmbH & Co. KGaA, Paul Schmidt et al (2003)" according to the invention.

Figure 5:
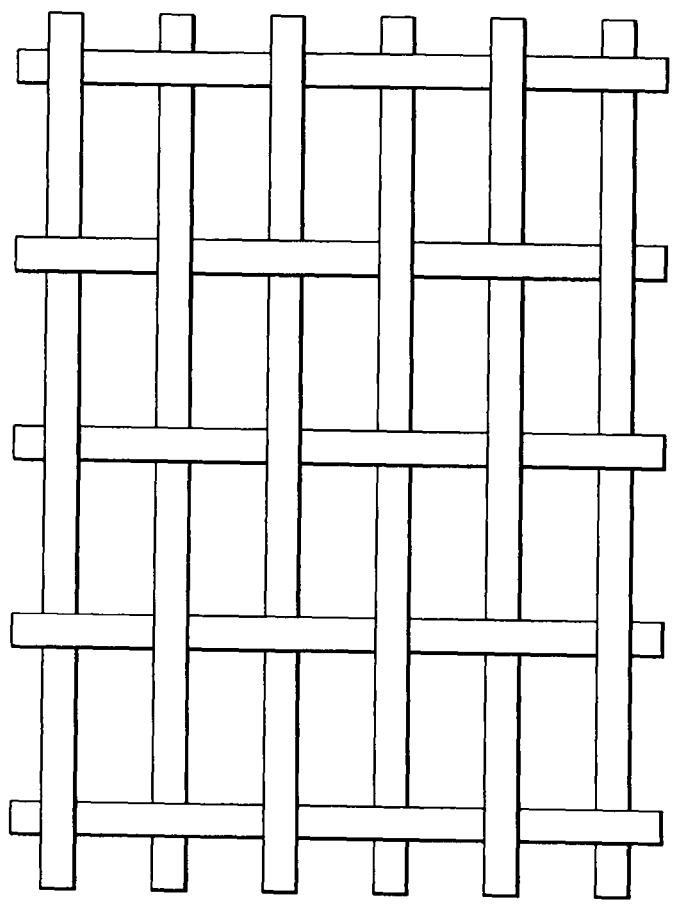
FIG. 5 illustrates a screen fabric having rectangular screen orifices.

Grids or grilles and screen fabrics (both ensure particularly high specific screen outputs in kg/m³ h at high efficacy) are suitable especially in the case of screen plates having only one inventive type of rectangular screen orifice. An exemplary illustrative depiction of such a screen fabric is shown by FIG. 5 of this document.

Figure 6:
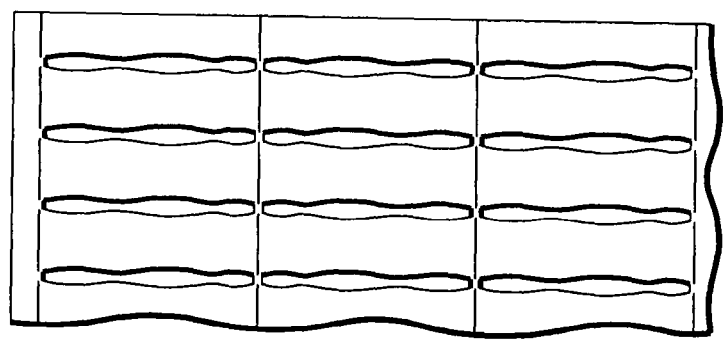
FIG. 6 illustrates a grid or grille having irregularly shaped orifices.

An exemplary illustrative depiction of such a grid or grille is shown by FIG. 6 of this document.

Any screen orifices suitable in accordance with the invention (or outlines of screen orifices) can be realized in a simple manner in perforated or slotted sheets. However, perforated or slotted sheets advantageous in accordance with the invention are especially those which have only one type of rectangular (or square) screen orifice (or outline thereof) or a screen orifice (or outline thereof) having an elongated hole shape.

Figure 9:
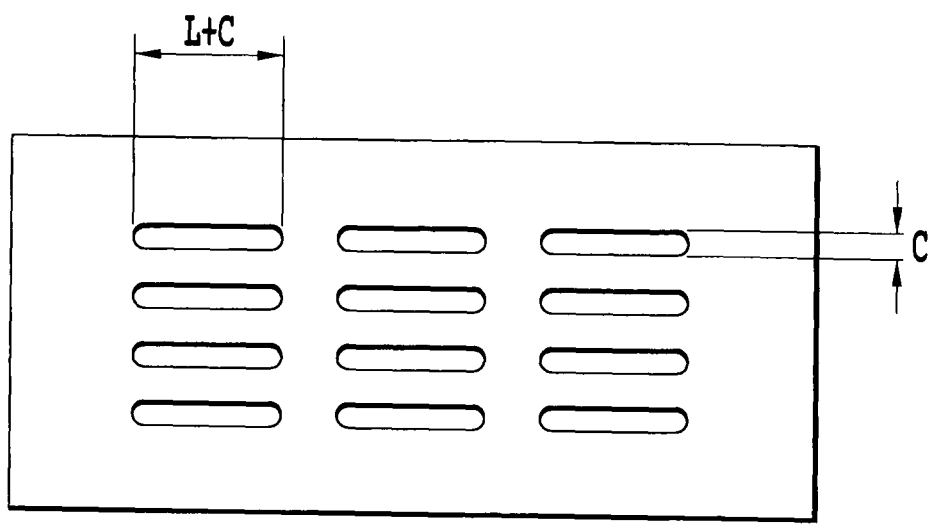
FIG. 9 illustrates a slotted sheet having orifices of an elongated hole shape in a straight line arrangement.
Figure 10:
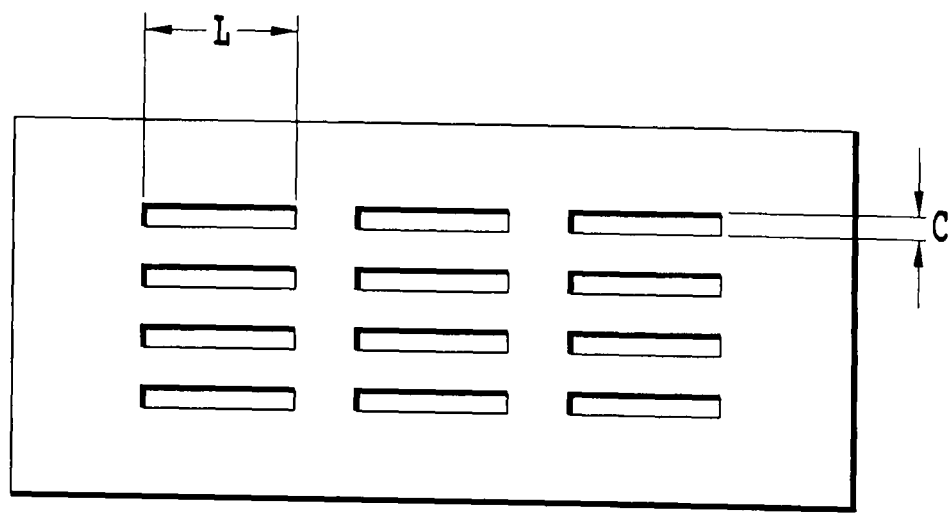
FIG. 10 illustrates a slotted sheet having rectangular orifices in a straight line arrangement.
Figure 11:
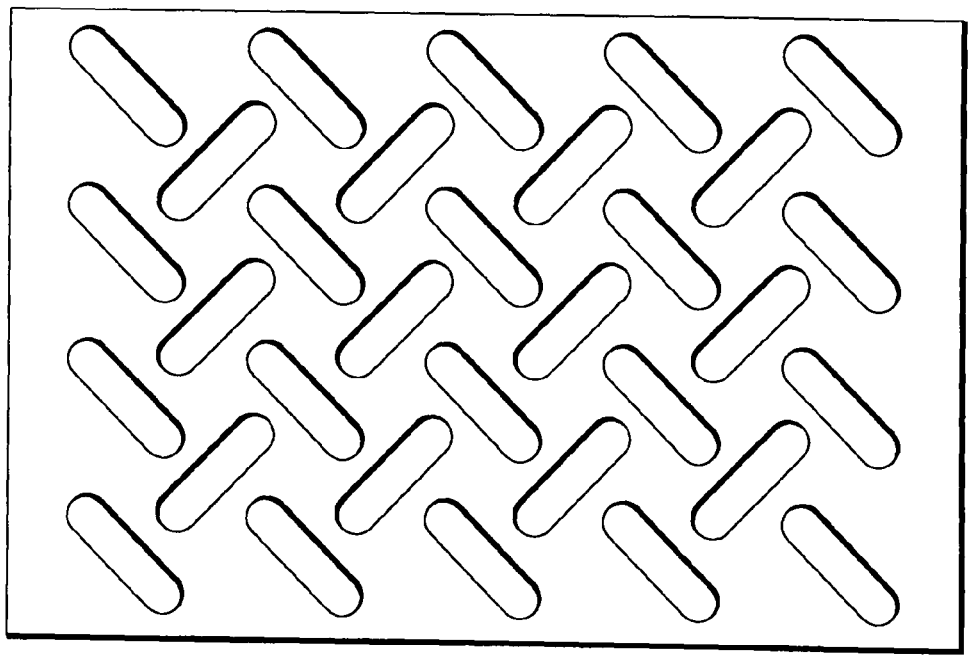
FIG. 11 illustrates a slotted sheet having orifices of an elongated hole shape in a fishbone-like arrangement.

What is particularly advantageous about perforated or slotted sheets is that the relative arrangement of screen orifices suitable in accordance with the invention is possible in virtually any manner. When the slotted sheet has only one type of rectangular (or square) screen orifice or a screen orifice having an elongated hole shape useful relative arrangements thereof in the slotted sheet for the process according to the invention are especially the mutually offset screen orifice arrangement according to FIG. 7, the overlapping offset screen orifice arrangement according to FIG. 8 (which is very particularly preferred in accordance with the invention (for reasons of stability among others)), the screen orifice arrangement in straight lines according to FIGS. 9 and 10, or fishbone-like screen orifice arrangements according to FIG. 11. A reason for a further advantage of slotted sheets is that they can be cleaned more easily in the case of product switches and are less prone to blockage of the screen orifices by stuck particles. They also generally have a higher mechanical stability.

Otherwise, perforated sheet screens (and slotted sheet screens) suitable in accordance with the invention can be configured as described in DIN 24041.

Typical sheet thicknesses d of perforated sheet screens (or slotted sheet screens) usable in accordance with the invention are from 1 to 5 mm, preferably from 1 to 3 mm, more preferably from 2 to 3 mm.

The open screen area F (the total (cross-sectional) area of all screen orifices present in a slotted sheet screen plate) of slotted sheet screen plates favorable in accordance with the invention will, based on the total area of the slotted sheet screen plate, typically be from 10 to 60%, preferably from 20 to 50% and more preferably from 30 to 50%.

Figure 7:
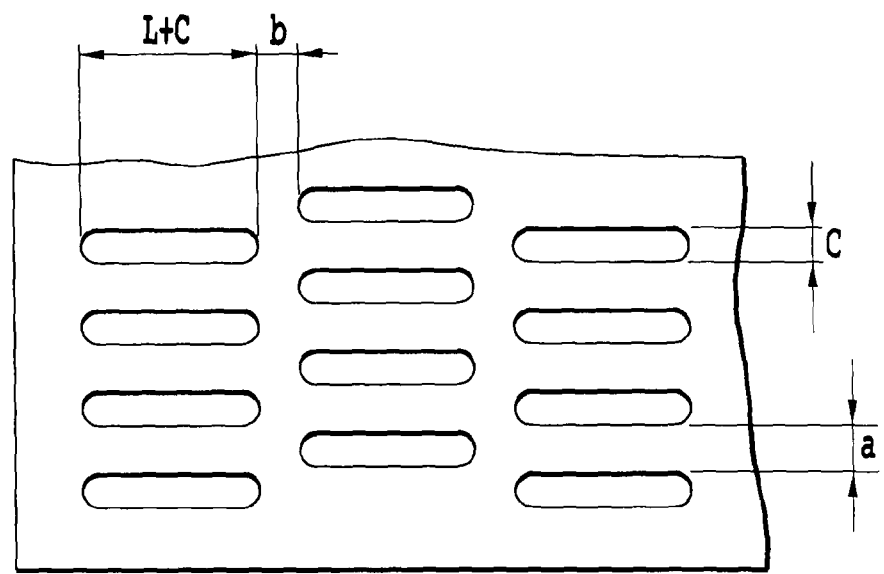
FIG. 7 illustrates a slotted sheet having orifices of an elongated hole shape in a mutually offset arrangement.

A sheet with elongated holes suitable in accordance with the invention (a screen plate with elongated holes suitable in accordance with the invention) with mutually offset elongated holes according to FIG. 7 may, for example, have the following configuration variants:

| Hole width C (mm) | Length L (mm) | Distance a (mm) | Distance b (mm) | d (mm) | F (%) |
|---|---|---|---|---|---|
| 1.0 | 19 | 3.0 | 5.0 | 1.5 | 19.8 |
| 1.6 | 18.4 | 2.4 | 5.0 | 1.0 | 31.4 |
| 2.0 | 18 | 10 | 4.5 | 1.25 | 13.3 |
| 2.5 | 17.5 | 3.5 | 5.0 | 1.0 | 32.4 |
| 4.0 | 6.0 | 7.0 | 4.0 | 2.0 | 23.7 |
| 5.0 | 20.0 | 4.0 | 5.0 | 2.0 | 45 |
| 5.0 | 15.0 | 3.0 | 5.0 | 2.0 | 47 |
| 5.0 | 15.0 | 4.0 | 5.0 | 2.0 | 42 |
| 8.0 | 17.0 | 8.0 | 11 | 2.0 | 32 |
| 10.0 | 22.0 | 6.0 | 8.0 | 2.0 | 47 |

Useful materials are especially steel (for example DIN materials 1.4541 or 1.4571 and S185 steel (DIN material 1.0035) according to DIN EN 10025 or DIN EN 10088-1).

Figure 8:
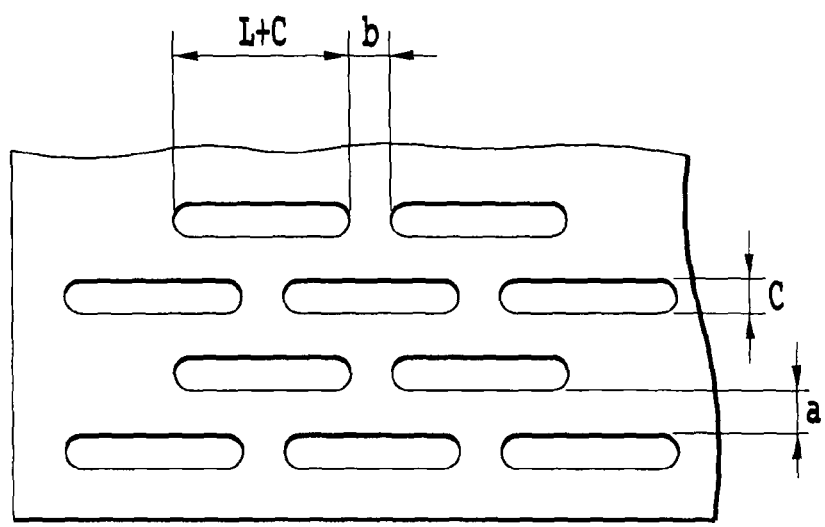
FIG. 8 illustrates a slotted sheet having orifices of an elongated hole shape in an overlapping offset arrangement.

A screen with elongated holes suitable in accordance with the invention with overlapping offset elongated holes according to FIG. 8 may, for example, have the following configuration variants:

| Hole width C (mm) | Length L (mm) | Distance a (mm) | Distance b (mm) | d (mm) | F (%) |
|---|---|---|---|---|---|
| 1.0 | 9 | 2.0 | 4.0 | 1 | 24 |
| 2.0 | 10.5 | 3.0 | 5.5 | 1 | 27 |
| 2.0 | 18.0 | 3.0 | 5.0 | 1 | 31 |
| 4.0 | 18.0 | 3.0 | 5.0 | 1 | 44 |
| 8.0 | 17.0 | 8.0 | 11 | 1 | 32 |

A useful material is especially steel (for example DIN materials 1.4541 or 1.4571).

In the case of annular coated catalysts K of geometry E×I×H=7 mm×4 mm×3 mm, suitable screens for an inventive screening-off of adhering pairs of coated catalyst rings are, for example, screens with elongated holes of the type described above (especially with an overlapping offset screen orifice arrangement) with C=5.50 mm and L=14.1 mm.

The sheet thickness may, for example, be 2.2 mm.

The bridge width a between elongated holes is, appropriately from an application point of view, 4.0 mm, and the distance b between two successive elongated holes on a common longitudinal line is advantageously 5.0 mm. The open screen area F is in this case 36.5%.

In the performance of an inventive screening-off, the material being screened is transported through a screen plate suitable in accordance with the invention, advantageously in accordance with the invention parallel to the preferential direction L of the inventive screen orifices. In a corresponding manner, the material being screened is also applied to the screen (to the screen plate) with this direction of application.

When the screen plate used in accordance with the invention is a perforated sheet with punched screen orifices, the punched burr is generally removed and the outline of the screen orifices is, appropriately from an application point of view, rounded off. Over the screen plate thickness, the cross section of a screen orifice is normally essentially constant (i.e. the orifice generally has a constant passage cross section). When the punched burr is not removed, it normally points in the direction of the screen passage.

In principle, the material being screened can be transported through the screen in a screening process according to the invention through a circular, elliptical and/or linear vibrating motion of the screen plate. For this purpose, for a screening process according to the invention, it is possible in principle to use all screening machines recommended, for example, in Chem.-Ing.-Tech. 56 (1984) No. 12, p. 897 to 907, and also in Sieben und Siebmaschinen, Grundlagen und Anwendung [Screens and Screening Machines, Fundamentals and Use], Wiley VCH, Paul Schmidt (2003). Also useful for a screening process according to the invention are the screening machines of the multideck design described in the documents DE-A 3520614, EP-A 205089 and DE-A 3431337, and those described in Aufbereitungstechnik 42 (2001) No. 7, page 345 to 348 and in Aufbereitungstechnik 41 (2000) No. 7, page 325 to 329.

A group of screening machines suitable for performing a process according to the invention is that of the planar screens in which the material being screened slides as a mat of material being screened in a linear or circular motion on the screen (the screen plate). The intrinsic weight and the friction against the screen cause shearing of the mat of material being screened. What is advantageous is the very low backmixing, which usually has an adverse effect.

The vibrating motion of the screen surface in the case of planar screens is effected in their screen plane. The vibrating motion may have a linear (to and fro) or circular profile (in the first case, reference is made to a linear planar vibrating screen). In the former case, it can proceed in conveying direction or transverse to it. Asymmetric acceleration in the case of linear vibrating motion in conveying direction, even in the case of a horizontal screen, can bring about longitudinal transport of the material being screened.

The circular vibration offers the advantage of constantly maintaining optimal acceleration. It will be appreciated that it is also possible to employ a combination of linear and circular vibrators in the process according to the invention.

In circular vibrators, the horizontal circulating motion is frequently generated through a geared motor. In linear vibrators, the whole screen frame (in which the screen plate is normally quite generally mounted) is set into a linear motion by contrarotatory unbalanced masses. Linear vibrators may be employed either with a horizontal or inclined screen plate. In the case of a inclined screen plate, the material being screened, by virtue of appropriate inclined inclination of the plane of vibration relative to the screen plate, in accordance with a parabolic trajectory, is thrown upward and simultaneously forward. The angles of inclination may, for example, be from −3° to 25°. From 3° to 4° are preferred in accordance with the invention. Suitable in accordance with the invention are, for example, linear vibration screens from Rhewurm GmbH in Remscheid, Germany.

Rectangular screening machines are generally preferred over round screens for an inventive planar screening operation. In the case of these, normally rectangular screen plates are introduced into a likewise rectangular screen frame.

Advantageously, for an inventive screen removal, an arrangement of screen plates one on top of another is employed, as is customary, for example, in the case of the screening machines of the multideck design already mentioned.

In this case, appropriately in accordance with the invention, the adhering pairs of coated catalyst rings (and any other multiple coated catalyst rings) will, in the inventive manner, be removed at least partly as screen residue with the uppermost screen. The desired coated catalyst rings K and any more finely divided constituents of the material being screened compared to the coated catalyst rings K are, in contrast, passed through from the uppermost screen plate to the screen plate below. Its screen orifices may, for example, following the teaching of U.S. Pat. No. 7,147,011 and of EP-A 1726358, be configured such that the coated catalyst rings K form the screen residue (the oversize) and the finely divided constituents of the material being screened form the material which passes through the screen (the undersize). Alternatively to the teaching of U.S. Pat. No. 7,147,011 and of EP-A 1726358, with regard to an annular coated catalyst K with the geometry E×I×H with the proviso that E≧H and with the aim of obtaining the annular coated catalysts K as oversize, it is also possible for the screen orifices of the screen plate to be configured such that their continuous outline has in each case at least two straight-line sections which are opposite one another at a distance C* over at least one length L* like two parallel sides of a rectangle with the side lengths L* and C*, with the proviso that each parallel line, running through an outline point P lying on the outline of a screen orifice, to the theoretical rectangle side with the side length C* does not have any further point lying on the outline whose distance from the outline point P is >C* and, at the same time, the relations L*>E≧H>C*≧(E−I)/2 are satisfied.

In the case of a successive arrangement of screen plates, both round screens and rectangular screens can be used. The vibrating motion is preferably configured such that the screen residue is in each case transported to the periphery of the round screen or rectangular screen and discharged there.

In the case of an inventive use of screening machines of the multideck design already addressed, a Mogensen Sizer® will advantageously be employed.

The system of a Mogensen—(for example one of the "SZ 0534" type suitable for an inventive removal, on a 04711 machine, built in 1997) consists of at least two normally differently inclined screen decks which are arranged one on top of another with screen orifices decreasing in the downward direction and increasing angles of inclination (to the horizontal). In general, the angle of inclination is in the range from 5 to 30°. For the inventive requirements, the use of a Mogensen Sizer with two screen decks is typically sufficient. The upper of the two screen decks accomplishes the inventive removal of adhering pairs and the screen deck which follows below it can remove the annular coated catalysts K from more finely divided constituents of the material being screened as screen oversize. Caused by the different inclination of the screen plates (screen linings), their screen orifices act like screen orifices of a smaller size. Therefore, compared to flat screens, the screen orifices can be selected with a comparatively larger size with essentially equally good separating efficiency, which enables increased specific screen outputs. It is characteristic of a Mogensen Sizer that the material being screened is initially loosened up and then flows through the individual screen decks almost vertically in free fall. The coarse fractions obtained are each collected in an outlet of the sizer and conducted out of the sizer via an outlet stub assigned to the outlet. Comprehensive details of Mogensen Sizers can be found, for example, in Aufbereitungstechnik 42 (2001) No. 7, page 345 to 348, and in Aufbereitungstechnik 41 (2000) No. 7, page 325 to 329, and the literature cited in these two documents, but also in DE-A 3520614, EP-A 205089 and in DE-A 3431337.

In the preparation of annular coated catalysts K with an annular geometry E×I×H=8 mm×5 mm×6 mm, it is possible, for example, for the inventive removal of adhering pairs to use a two-deck Mogensen Sizer of the SZ 0534 type (machine 04711) with two rectangular screen decks (e.g. length 1340 mm and width 490 mm). The distance between the two screen plates lies in the vertical, for example at a maximum value of 130 mm. The screens used are, in a manner appropriate in accordance with the invention, screening fabric according to FIG. 5, but with square screen orifices in the case of the upper screen deck (the geometry of the outline of the screen orifices of the upper screen deck is advantageously 10 mm×10 mm and the geometry of the outline of the screen orifices of the lower screen deck is advantageously 6 mm×130 mm; the thickness of the woven steel wire is typically from 1.5 to 1.7 mm; the inclination of the upper screen plate to the horizontal is appropriately 10° and that of the lower screen plate appropriately 20°; typical throughputs of material being screened are from 300 to 350 kg/h; later in this document, such a Mogensen Sizer is also referred to as a "Mogensen Sizer I").

When the annular coated catalysts K prepared have the annular geometry E×I×H=7 mm×4 mm×7 mm, it is possible for an inventive removal of adhering pairs to use a correspondingly constructed Mogensen Sizer. The geometry of the outline of the screen orifices of the upper screen deck is, however, advantageously 8 mm×8 mm and the geometry of the outline of the screen orifices of the lower screen deck is advantageously 5 mm×130 mm. This Mogensen Sizer shall be referred to in this document as "Mogensen Sizer II".

While, in the case of an inventive removal with the aid of a Mogensen Sizer, no screening assistant introduced between the two screen decks is used in order to keep the upper and the lower screen plate continuously free of stuck particles, it is generally appropriate in the case of a predominantly horizontal screen surface to use rubber ball knocking for this purpose (cf. FIG. 12 in Chem.-Ing. Tech. 56 (1984) No. 12, page 902). In this method, rubber balls are placed onto a blank plate which is at a distance Z of 1.2- to 1.5 times the rubber ball diameter below the actual screen (screen plate). The rubber balls, even in the case of planar screening machines, jump from below against the screen and clean it locally during the screening operation (during the screening). Their elasticity is advantageously such that they essentially do not cause any fracture of the material being screened. The blank plate is usually a perforated sheet with preferably square hole orifices. In each case, the hole orifices of the blank plate are such that the material passing through the screen can pass through it.

Advantageously from an application point of view, screen plates (as the "top plane") and blank plates (as the "base plane") are equipped with identical cross-sectional area and are supplemented by four side walls of height Z to form a cuboidal side insert which can be inserted in a simple manner into the screen frame (the frame height projects beyond the screen insert inserted generally by about 10 cm). Alternatively to rubber ball knocking, screen cleaning can also be brought about during the screening operation by means of flat or roller brushes arranged above and/or below the screen plate.

The preparation of annular coated catalysts K and an inventive screen removal can be performed either spatially separately or spatially merging directly into one another. The latter is appropriate, for example, when the preparation of the annular coated catalysts K is effected as described in DE-A 2909671, DE-A 102005010645, EP-A 714700, DE-A 10325488, DE-A 10360058, WO 2004/108267 and German application 102007010422.9.

In these preparation processes, the annular shaped support body is first moistened with a liquid binder, then a layer (coating) of the aforementioned finely divided composition is adhered on the surface of the moistened annular shaped support body by contacting with finely divided, dry catalytic active composition (for example multielement oxide composition) and/or finely divided dry precursor composition of the catalytic active composition, and then the liquid binder is at least partly volatilized from the annular shaped support body coated with the finely divided composition under the action of heat, and any precursor composition present in the coating is converted to the active composition by thermal treatment. In this document, this preparation method is referred to as the "coating process".

Useful liquid binders are in particular all of those which are detailed in DE-A 10 2005 010645 and in EP-A 714700.

These include in particular inorganic and organic liquids, and also mixtures of inorganic and organic liquids.

Examples include water, monohydric alcohols, for example methanol and ethanol, polyhydric alcohols, for example ethylene glycol (or simply glycol) and glycerol, ethers of aforementioned mono- and polyhydric alcohols (e.g. diethyl ether, dibutyl ether and glycol diethyl ether), esters of organic carboxylic acids and the aforementioned mono- and polyhydric alcohols, for example ethyl acetate, organic carboxylic acids themselves, for example acetic acid, organic amines, organic amides, amino alcohols (e.g. ethanolamine), hydrocarbons, for example gasoline, solutions of inorganic salts in water and/or organic alcohols, solutions of organic fatty acids in water, solutions of mono- and oligosaccharides in water, mixtures of different portions of the aforementioned liquids, but also solutions of polymers and dispersions of polymers.

Preferred liquid binders are solutions which consist of water to an extent of from 20 to 90% by weight and of an organic compound dissolved in water to an extent of from 10 to 80% by weight. The organic proportion in the aqueous solution to be used as a binder is preferably from 10 to 50% by weight, more preferably from 20 to 30%. Suitable organic components of liquid binder are in particular mono- and polyhydric organic alcohols such as glycol, 1,4-butanediol, 1,6-hexanediol and glycerol, mono- or polybasic organic carboxylic acids such as propionic acid, oxalic acid, malonic acid, glutaric acid and maleic acid, amino alcohols such as ethanolamine or diethanolamine, mono- or polyfunctional organic amides such as formamide, or monosaccharides and oligosaccharides such as glucose, fructose, sucrose or lactose. One reason for the advantageousness of such solutions as a liquid binder is that they are generally capable of wetting both the annular support bodies and the finely divided composition to be applied to them. Useful materials for the annular shaped support bodies include all materials mentioned in this document and all of those mentioned in German application 102007010422.9, in DE-A 10 2005 010 645 and in EP-A 714 700. These include especially aluminum oxide, silicon dioxide, silicates such as clay, kaolin, steatite, pumice, aluminum silicate and magnesium silicate, silicon carbide, zirconium dioxide and thorium dioxide.

Advantageously, the surface of the annular shaped support body is rough (as recommended in the three documents above), since an increased surface roughness generally causes an increased adhesion strength of the coating of active composition and/or precursor composition applied on the surface of the annular shaped support body.

Furthermore, the support material is preferably nonporous (total volume of the pores based on the volume of the support body $\leq 1\%$ by volume).

For a performance of the above-described process for preparing annular coated catalysts K, a suitable process principle is in particular that disclosed in DE-A 2909671 (see also EP-A 714 700 and DE-A 10 2005 010 645) using the liquid binder desired in each case.

In other words, the annular shaped support bodies to be coated are filled into a preferably inclined (the angle of inclination is generally from 30 to 90°) rotating vessel (for example rotating pan or coating tank or coating drum). Favorable rotary vessels for this end use are especially the Hi-Coater HCF-100 from Freund Industrial Co., Ltd, Tokyo (Japan) and the Hi-Coater LH 100 from Gebrüder Lödige Maschinenbau GmbH, Paderborn, Germany.

The rotating vessel conducts the annular shaped support bodies under two metering devices which are arranged in succession at an advantageous distance. The first of the two metering devices corresponds appropriately to a nozzle by which the annular shaped support bodies rolling in the rotating pan (Hi-Coater) are moistened in a controlled manner with the liquid binder. The second metering device is, appropriately from an application point of view, disposed outside the atomization cone of the sprayed liquid binder and serves to supply the finely divided active composition (for example a finely divided multielement oxide active composition) and/or the finely divided precursor composition (for example by means of a shaking channel). The annular shaped support bodies moistened in a controlled manner take up the finely divided composition (the finely divided powder) supplied, which is compacted by the rolling motion on the outer surface of the annular shaped support body to form a coherent coating (such a compacting motion does not take place in the inner circle of the annular shaped support bodies, which is why it remains essentially uncoated).

If required, the annular shaped support body base-coated in this way, in the course of the subsequent rotation, again passes through the spray nozzle, is moistened in a controlled manner (if appropriate with another liquid binder) as it does so, in order to be able to take up a further layer of (an optionally different) finely divided active composition and/or precursor composition in the course of the further motion, etc. (intermediate drying is generally not required). The at least partial removal of the liquid binder used can, for example, following the teaching of EP-A 714 700 or the teaching of DE-A 10 2005 010 645, be effected by final heat supply, for example by the action of hot gases such as $N_2$ or air (these are supplied and removed through spatially separately mounted wall elements, configured in a mesh-like manner, of the rotary pan, of the coating tank or of the coating drum (in general, rotary vessel)).

What is of significance for the embodiment of the coating process described is that the moistening of the annular shaped support bodies to be coated is undertaken in a controlled manner. In short, this means that the support surface is appropriately moistened such that it has adsorbed liquid binder, but it does not appear visually on the support surface. When the shaped support body is too moist, the finely divided active composition and/or precursor composition agglomerates to form separate agglomerates instead of attaching to the surface. More detailed information on this subject can be found in DE-A 2909671, in EP-A 714 700 and in DE-A 10 2005 010 645. The latter is especially also true for the final at least partial removal of the liquid binder used. This is because a further advantage of the procedure described consists in the ability to undertake this removal in a comparatively controlled manner, for example by evaporation and/or sublimation. In the simplest case, this can, as already stated, be effected through the action of hot gases of appropriate temperature (frequently from 50 to 150° C.). Such an action of hot gases can bring about either complete drying or only a predrying. The end drying can then be effected, for example, in a drying device of any type (for example in a conveyor belt drier) and/or not until within the fixed catalyst bed of the tube bundle reactor, as recommended, for example, by DE-A 10 2005 010 645.

The transition to an inventive removal of adhering pairs by screening can be configured in a simple manner, for example as follows. The production charge of annular coated catalyst disposed in the rotary vessel can be emptied through a funnel by opening an emptying flap disposed above the funnel. The discharge of the funnel is then continued directly into a (discharge) tube slightly inclined relative to the horizontal (the angle of inclination may, for example, be from −3° to 25°; from 3° to 5° are preferred).

The discharge tube typically has a length of 1200 mm and an internal diameter of, for example 100 mm. Otherwise, it is configured as a linear vibratory screen. For this purpose, it comprises an installed screen plate which extends over the entire tube length and divides the tube interior into an upper half-tube (above the screen plate) and into a lower half-tube (below the screen plate). As a result of tumbling motions of the rotary vessel, the production charge present in the rotary vessel empties into the upper half-tube of the discharge tube comprising the screen plate.

In the discharge tube, it is transported to its end (typically: 80 kg of coated catalyst rings per 30 minutes). On the route of the production charge through the discharge tube, the inventive removal of adhering pairs takes place by means of the screen plate of the discharge tube. The desired annular coated catalysts K form the material which passes through the screen, while the adhering pairs removed are discharged from the upper half-tube at the end thereof.

When the annular coated catalysts K are those of geometry E×I×H=7 mm×4 mm×3 mm, the screen plate used in the aforementioned discharge tube will advantageously be a screen with overlapping crosslinked elongated holes according to FIG. 8. Advantageously in accordance with the invention, C=5.50 mm and L=14.1 mm. A sheet thickness of 2.2 mm is just as advantageous as a bridge width a of 4.0 mm and a distance b of 5.0 mm. The open screen area F is in this case 36.5%.

A Hi-Coater of the LH 100 type from Gebrüder Lödige Maschinenbau GmbH, Paderborn, Germany, which has a discharge tube for removing adhering pairs as just described, will be referred to in this document as a "removal Hi-Coater I".

The adhering pairs of coated catalyst rings removed in accordance with the invention are generally not disposed of but rather reprocessed. In other words, it will typically be attempted to recover the elements present in the active composition thereof.

An inventive screen removal is generally performed under air (especially in the case of all multielement oxide catalysts listed by way of example in this document).

In the case of strongly hygroscopic or oxygen-sensitive coated catalysts K or active compositions thereof, adhering pairs can also be screened off with exclusion of moisture and/or oxygen (e.g. under $N_2$). Before the screen removal, the annular shaped coated catalyst bodies K are generally supplied directly to a vessel which can be closed air-tight, in which they can be stored. From this vessel (for example a vat lined with a polypropylene shell), they can then be withdrawn, for example for the purpose of a structured filling of reaction tubes, following the teaching of DE-A 10 2004 023 249, and be introduced into the reaction tube contemplated.

Alternatively to the coating process for preparing coated catalysts K, coated catalysts K will frequently also be prepared by spraying the annular shaped support bodies with a suspension of finely divided active composition and/or finely divided precursor composition.

Advantageously in accordance with the invention, the procedure will be as described in DE-A 4006935 and DE-A 10344844. The suspension, for example aqueous suspension, of the finely divided active composition and/or finely divided precursor composition which, in order to improve the quality of the coating of the annular shaped support bodies, generally comprises added organic binders (generally copolymers, for example those based on vinyl acetate/vinyl laurate, or on vinyl acetate/acrylate, or on styrene/acrylate, or on vinyl acetate/ethylene) (for example in the form of an aqueous polymer dispersion) is sprayed at elevated temperature onto the annular shaped support bodies until the desired active composition content in the total catalyst weight has been attained. Suitable apparatus for this purpose is especially fluidized bed and moving bed apparatus. In this apparatus, the annular shaped support bodies are fluidized in an ascending gas stream (for example hot air). The apparatus usually consist of a conical or spherical vessel in which the fluidizing gas is introduced from the bottom or from the top via a central tube. The suspension is sprayed into the fluidized bed of the annular shaped support bodies via nozzles from the top, laterally or from the bottom. It is advantageous to use a guide tube arranged in the middle or concentrically around the central tube. Within the central tube, there is a higher gas velocity, which transports the annular shaped support bodies upward. In the outer ring, the gas velocity is only slightly above the fluidization velocity. Thus, the annular shaped catalyst supports are moved in a vertical circular motion. Further details of this "spray process" for preparing annular coated catalysts K can be found, for example, in DE-A 10344844 and in DE-A 4006935. The latter also discloses a moving bed apparatus which is particularly suitable in this regard.

Moreover, a production charge of coated catalysts K in the context of this invention is a production amount of coated catalyst K which is capable of covering the demand of at least two (better at least 10, frequently at least 50, usually at least 100, in many cases at least 200 or at least 500) reaction tubes in the tube bundle reactor.

Annular coated catalysts K comprise, among other catalysts, those coated catalysts whose active composition is a multielement oxide of the general formula I $$Mo_{12}Bi_aFe_bX_c^1X_d^2X_e^3O_y \qquad (I)$$

where
$X^1$=Co and/or Ni,
$X^2$=Si and/or Al,
$X^3$=Li, Na, K, Cs and/or Rb,
$0.2 \leq a \leq 1$,
$2 \leq b \leq 10$,
$0.5 \leq c \leq 10$,
$0 \leq d \leq 10$,
$0 \leq e \leq 0.5$, and
y=a number which (with the prerequisite of charge neutrality) is determined by the valency and frequency of the elements in I other than oxygen.

Such annular coated catalysts K can advantageously be prepared according to the teaching of DE-A 100 49 873. To this end, an intimate dry mixture is obtained from starting compounds of the elemental constituents of the catalytically active oxide composition and is treated thermally at from 150 to 350° C. to obtain a precursor composition. In the coating process, using water as a binder, a layer of the precursor composition is adhered to the annular shaped support bodies and the coated annular shaped support bodies, which are dry to the touch, are subsequently calcined at from 400 to 600° C.

These coated catalysts are suitable especially for the catalytic gas phase partial oxidation of propylene to acrolein and of isobutene to methacrolein. Advantageous partial oxidation conditions can likewise be found in DE-A 10049873.

The process according to the invention is also relevant in the preparation of annular coated catalysts K which have, as an active coating, a multielement oxide which comprises the element V, Sb and at least one element from Mo and W.

The preparation of such coated catalysts K is disclosed, for example, by WO 2007/00922. Here too, a preferred preparation process is the precursor composition coating process. However, it is equally possible to employ the active composition coating process. Such coated catalysts K are suitable especially for heterogeneously catalyzed partial ammoxidations of organic starting compounds. Examples thereof are the preparation of methylbenzonitriles and benzodinitriles from xylene. Favorable partial ammoxidation conditions in this regard are likewise disclosed by WO 2007/009922.

The process according to the invention is also of particular significance when the catalysts are those annular coated catalysts K whose catalytically active coating is a multielement oxide active composition of the general formula II

$$Mo_{12}V_aX_b^1X_c^2X_d^3X_e^4X_f^5X_g^6O_n \qquad (II)$$

where
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals (Li, Na, K, Rb, Cs) and/or H,
$X^5$=one or more alkaline earth metals (Mg, Ca, Sr, Ba),
$X^6$=Si, Al, Ti and/or Zr,
a=1 to 6,
b=0.2 to 4,
c=0 to 18, preferably 0.5 to 18,
d=0 to 40,
e=0 to 2,
f=0 to 4,
g=0 to 40, and
n=a number which is determined by the valency and frequency of the elements in II other than oxygen.

They are suitable in particular for a heterogeneously catalyzed partial gas phase oxidation of acrolein to acrylic acid. Advantageously, the annular coated catalysts are obtainable here by the process of DE-A 10 2005 010645, of DE-A 10325488, of DE-A 10360058, of DE-A 10350822, of DE-A 10 2004 025 445, of DE-A 10 2007 010 422, of US 2006/0205978 and of EP-A 714 700, and the processes of the prior art cited in these documents. A particularly preferred preparation process is the active composition coating process according to EP-A 714 700. According to German application 102007010422.9, it is possible to additionally add finely divided molybdenum oxide to the active composition applied in order to prolong the lifetime. The aforementioned documents additionally disclose particularly favorable conditions for a heterogeneously catalyzed partial gas phase oxidation of acrolein to acrylic acid.

The active composition coating thickness here will in particular be from 10 to 1000 μm, preferably from 50 to 500 μm and more preferably from 150 to 250 μm. Particularly favorable embodiments are the exemplary embodiments of EP-A 714 700. A preferred ring geometry is that where E×I×H=7 mm×4 mm×3 mm.

The process according to the invention is also of particular relevance in the case of annular coated catalysts K whose active composition is a multielement oxide which, has elements other than oxygen, as well as the elements Mo and V, comprise at least one of the two elements Te and Sb and at least one of the elements from the group comprising Nb, Pb, Ta, W, Ti, Al, Zr, Cr, Mn, Ga, Fe Ru, Co, Rh, Ni, Pd, Pt, La, Bi, B, Ce, Sn, Zn, Si, Na, Li, K, Mg, Ag, Au and In in combination.

Their preparation is disclosed, for example, by WO 2004/108267. They are suitable, inter alia, as catalysts for the heterogeneously catalyzed partial gas phase oxidation of acrolein to acrylic acid, of propane to acrolein and/or acrylic acid, of isobutane to methacrolein and/or methacrylic acid and for the ammoxidation of propane to acrylonitrile and of isobutane to methacrylonitrile (see also DE-A 10 2007 025 869).

However, the process according to the invention should also be employed in the case of annular coated catalysts K whose active composition comprises elemental silver on oxidic annular support bodies. Such annular coated catalysts K are suitable especially for a heterogeneously catalyzed partial gas phase oxidation of ethylene to ethylene oxide (cf., for example, EP-A 496 470). Useful shaped support bodies are in particular those which consist to an extent of at least 80% by weight of aluminum oxide (e.g. $Al_2O_3$). As supported catalysts for a heterogeneously catalyzed partial gas phase oxidation of ethylene to ethylene oxide which comprise elemental silver in their active composition applied to an oxidic annular shaped support body, the annular supported catalyst of EP-A 619 142, EP-A 624 398, EP-A 804 289 and EP-A 937 498 should also be emphasized. For all of these annular coated catalysts K, the process according to the invention is a suitable option.

Favorable ring geometries E×I×H include the ring geometries 8.5 mm×3.2 mm×8.5 mm, and 8.5 mm×3.4 mm×8.5 mm and 8 mm×3 mm×8 mm or 7.7 mm×3 mm×5 mm.

The process according to the invention also has increased relevance in the case of annular coated catalysts K whose active composition is at least one multielement oxide which comprises oxidic $TiO_2$ units to an extent of at least 60% by weight but to an extent of not more than 99% by weight, and oxidic $V_2O_5$ units to an extent of at least 1% by weight but to an extent of not more than 40% by weight. Frequently, the aforementioned multielement oxide active compositions also comprise up to 1% by weight of Cs, up to 1% by weight of P and up to 10% by weight of oxidic $Sb_2O_3$ units. In addition, they may comprise further promoters which promote the activity and selectivity of the coated catalyst K.

These annular coated catalysts K are suitable in particular for the heterogeneously catalyzed partial gas phase oxidation of aromatic hydrocarbons such as benzene, naphthalene, xylenes, toluene and/or durene. In this way, it is possible to obtain, for example, benzoic acid, maleic anhydride, phthalic anhydride, isophthalic acid, terephthalic acid and/or pyromellitic anhydride. A preferred preparation process for such annular coated catalysts K is the suspension spraying process. The preparation of such coated catalysts K and particularly favorable partial oxidation conditions are disclosed, for example, by DE-A 19839001, DE-A 10344844, DE-A 4006935, DE-A 19823262 and DE-A 19823275.

Favorable multielement oxide active compositions which comprise V and Ti and are suitable for such coated catalysts are also disclosed by the documents U.S. Pat. Nos. 6,528,683, 6,586,361 and 6,362,345, including favorable conditions for a heterogeneously catalyzed partial gas phase oxidation of o-xylene and/or naphthalene to phthalic anhydride (as always in this document, the term "partial oxidation conditions" also comprises the structuring (charging) of the fixed catalyst bed in the reaction tubes). Ring geometries of the coated catalysts K suitable for aforementioned partial oxidations are, for example, the ring geometries (E×I×H) 7 mm×4 mm×7 mm, 8 mm×5 mm×6 mm, 7 mm×4 mm×4 mm, 8 mm×4 mm×6 mm, and 8 mm×3 mm×6 mm.

The process according to the invention is also outstandingly suitable for the annular multielement oxide coated catalysts which comprise Mo and Fe, are disclosed in DE-A 10 2005 055 827 and are suitable especially for the oxidation of methanol to formaldehyde.

Otherwise, the fixed catalyst bed charging of the reaction tubes of the tube bundle reactor is as described in German application 102007017080.9.

EXAMPLES

A) Heterogeneously Catalyzed Partial Gas Phase Oxidation of Acrolein to Acrylic Acid in a Thermal Tube
I. Charging of a Thermal Tube with a Fixed Catalyst Bed Comprising Annular Coated Catalysts, a Removal of Adhering Pairs Having been Performed Before the Introduction of the Annular Coated Catalysts The thermal tube (V2A steel; external diameter 33.7 mm, wall thickness 2 mm, internal diameter 29.7 mm, length: 350 cm, and a thermowell centered in the middle of the thermal tube (external diameter 10 mm) for accommodating a stationary multithermoelement with which the temperature in the thermal tube can be determined over its entire length) was charged from the top downward as follows:

Section 1: length 20 cm steatite rings ST of geometry 7 mm×4 mm×3 mm (E×I×H) as a preliminary bed (C 220 steatite from CeramTec);

Section 2: length 90 cm fixed catalyst bed charge with a homogeneous mixture of 30% by weight of steatite rings ST, 30% by weight of annular coated catalysts K1 according to working example 2 of WO 2004/108267, but with preceding removal of adhering pairs (7.1 mm×4.0 mm×3.2 mm; $Mo_{12}V_3W_{1.2}Cu_{2.4}O_x$; the annular shaped support bodies are coated and the adhering pairs are removed with a Hi-Coater I) and 40% by weight of spherical coated catalysts KU1 (prepared like the annular coated catalysts K1, but with spherical shaped support bodies of steatite having a diameter of 4-5 mm, and using water as a binder and a proportion by weight of 20% by weight of the active composition coating;

Section 3: length 50 cm fixed catalyst bed charge with a homogeneous mixture of 20% by weight of steatite rings ST, 40% by weight of annular coated catalysts K1 (with preceding removal of adhering pairs) and 40% by weight of spherical coated catalysts KU1;

Section 4: length 70 cm fixed catalyst bed charge with a homogeneous mixture of 60% by weight of annular coated catalysts K1 (with preceding removal of adhering pairs) and 40% by weight of spherical coated catalysts KU1; and Section 5: length 120 cm fixed catalyst bed charge with only spherical coated catalyst KU1.

From the top downward, the first 175 cm were thermostatted by means of a salt bath A pumped in countercurrent, which was supplied with the temperature $T_H^A$. The second 175 cm were thermostatted by means of a salt bath B pumped in countercurrent, which was supplied with the temperature $T_H^B$. Both salt baths were a mixture of 53% by weight of potassium nitrate, 40% by weight of sodium nitrite and 7% by weight of sodium nitrate.

The above-described thermal tube was charged continuously with a reaction gas input mixture of the following contents:

4.8% by volume of acrolein,
0.5% by volume of acrylic acid,
0.2% by volume of propylene,
5.5% by volume of molecular oxygen,
0.5% by volume of CO,
1.1% by volume of $CO_2$,
5.7% by volume of water, and
81.5% by volume of nitrogen.

The reaction gas mixture flowed through the thermal tube from the top downward. The pressure at the inlet to the thermal tube was 2.0 bar (absolute). The loading of the fixed catalyst bed with acrolein was 140 l (STP)/l·h.

$T_H^A$ was adjusted to 275° C. and $T_H^B$ to 279° C. The reaction gas input mixture was preheated to 220° C.

At a conversion of the acrolein of approx. 99.5 mol % and a selectivity of acrylic acid formation of 95.0 mol % based on single pass of the reaction gas mixture through the thermal tube, the hotspot temperature in the thermal tube was 323° C. The position of the hotspot maximum was, in flow direction of the reaction gas, 45 cm after the start of section 2.

II. Repetition of the Partial Oxidation from A) I, but with Controlled Doping of the Fixed Catalyst Bed Introduced into the Thermal Tube with a Tandem Adhering Pair Obtained in the Course of Removal of Adhering Pairs in the Preparation of the Annular Coated Catalysts K1 (the Total Amount of Adhering Pairs Removed was 0.24% by Weight)

The fixed catalyst bed was charged as in A) I. In flow direction of the reaction gas, 45 cm after the start of section 2, however, a tandem adhering pair (0.02% by weight based on the total weight of annular coated catalysts K1 introduced) was positioned deliberately between the inner wall of the thermal tube and the outer wall of the thermowell such that its longitudinal axis pointed in the flow direction of the reaction gas. Otherwise, the procedure was as in A) I and the thermal tube charge was also conducted to the end in the same way.

With an unchanged position of the hotspot temperature, it was increased to 325° C.

III. Repetition of the Partial Oxidation from A) I, but with Controlled Doping of the Fixed Catalyst Bed Introduced into the Thermal Tube with a Fused Adhering Pair Obtained in the Course of Removal of Adhering Pairs in the Preparation of the Annular Coated Catalysts K1

The fixed catalyst bed was charged as in A) I. As the first 70 cm of reaction tube length viewed in flow direction of the reaction gas were still uncharged and the remaining reaction tube length had already been charged, a fused adhering pair was wedged (jammed) between the inner wall of the thermal tube and the outer wall of the thermowell 40 cm after the start of section 2 in flow direction. Otherwise, the procedure was as in A) I and the thermal tube filling, after the adhering pair had been wedged in, was also conducted to the end in the same way.

The position of the hotspot maximum was now as early as (in flow direction of the reaction gas) 40 cm after the start of section 2. It was now 324° C.

B) Heterogeneously Catalyzed Partial Gas Phase Oxidation of Acrolein to Acrylic Acid in a Working Tube (which is Represented by the Thermal Tube in A) I)

A working tube (V2A steel; external diameter 30 mm; wall thickness 2 mm, internal diameter 26 mm, length 350 cm) was charged as described above with a fixed catalyst bed comprising annular coated catalysts K1 (with preceding removal of adhering pairs). To determine the profile of the reaction temperature in the working tube, it comprised, introduced directly into the center, a multithermoelement (external diameter=4 mm; in the industrial scale tube bundle reactor, this procedure is not possible; an industrial scale working tube (which does not comprise a thermoelement) would therefore comprise a somewhat larger total amount of active composition overall and therefore require $T_H^A$, $T_H^B$ lower by 1° C. for the same acrolein conversion).

I Ideal Charge (without Adhering Pairs) of the Working Tube with the Fixed Catalyst Bed (from the Top Downward)
Section 1: length 20 cm steatite rings ST;
Section 2: length 90 cm homogeneous mixture of 70% by weight of annular coated catalysts K1 and 30% by weight of steatite rings ST;

Section 3: length 50 cm homogeneous mixture of 80% by weight of annular coated catalysts K1 and 20% by weight of steatite rings ST;

Section 4: length 190 cm only annular coated catalyst K1.

In this working tube, under the same conditions as in the thermal tube under A) I, a heterogeneously catalyzed partial gas phase oxidation of acrolein to acrylic acid was performed (for the reasons addressed above, $T_H^A=276°$ C. and $T_H^B=280°$ C. in order to achieve the same acrolein conversion of 99.5 mol %).

The hotspot temperature was 323° C. as in the thermal tube. The position of the hotspot maximum was, as in A) I, 45 cm after the start of section 2 in flow direction of the reaction gas.

II. In the Same Way as the Thermal Tube in A) II, the Fixed Catalyst Bed Charge of the Working Tube was Doped with a Tandem Adhering Pair.

As a result, a hotspot temperature of 325° C., increased by 2° C., was established with the same position of the hotspot maximum.

III. The Fixed Catalyst Bed Charge was Undertaken as in B) I, Except that, in the Portion of Annular Coated Catalysts 1 Forming Section 4, before it was Emptied into the Working Tube, a Tandem Adhering pair was Randomly Added (After the Addition, the Portion was Shaken).

The resulting partial oxidation results were indistinguishable from those in B) I under otherwise identical operating conditions.

C) Heterogeneously Catalyzed Partial Gas Phase Oxidation of o-xylene to Phthalic Anhydride in a Thermal Tube I. Charging of a Thermal Tube with a Fixed Catalyst Bed Comprising Annular Coated Catalysts, a Removal of Adhering Pairs Having Been Performed Before the Introduction of the Annular Coated Catalysts.

The thermal tube (V2A steel; internal diameter: 25 mm, wall thickness: 2 mm; length: 385 cm; a thermowell centered in the middle of the reaction tube (external diameter 4 mm) for accommodating a single thermoelement movable along the reaction tube in order to determine the reaction temperature along the reaction tube) was charged from the top downward as follows:

Section 1: length 10 cm steatite rings S(C 220 steatite from CeramTec) of geometry 5 mm×2 mm×3 mm (E×I×H);

Section 2: length 170 cm annular coated catalyst according to example 7 of DE-A10344844, but with removal of adhering pairs (suspension spray process; support geometry=8 mm×5 mm×6 mm (E×I×H); removal of adhering pairs by means of a Mogensen Sizer I; the multimetal oxide active composition coating comprised 0.08% by weight of P; 5.75% by weight of $V_2O_5$ units; 1.6% by weight of $Sb_2O_3$ units; 0.4% by weight of Cs and 92.17% by weight of $TiO_2$ units);

Section 3: length 130 annular coated catalyst according to example 4 of DE-A10344844, but with removal of adhering pairs (suspension spray process; support geometry=8 mm×5 mm×6 mm (E×I×H); removal of adhering pairs by means of a Mogensen Sizer I; the multimetal oxide active composition coating comprised 0.15% by weight of P; 7.5% by weight of $V_2O_5$ units; 3.2% by weight of $Sb_2O_3$ units; 0.1% by weight of Cs and 89.05% by weight of $TiO_2$ units).

The thermal tube was flowed around by a salt bath (a mixture of 53% by weight of potassium nitrate, 40% by weight of sodium nitrite and 7% by weight of sodium nitrate) which had a temperature of 350° C.

The above-described thermal tube was charged with a reaction gas input mixture composed of 2% by volume of o-xylene and 98% by volume of air.

The charge gas flow rate was 4 m³ (STP)/h at an inlet pressure of 1.4 bar (absolute). The reaction gas mixture flowed through the thermal tube from the top downward. At a conversion of the o-xylene, based on single pass of the reaction gas mixture through the thermal tube, of 99.97 mol %, the selectivity of phthalic anhydride formation was 81.7 mol %. The hotspot temperature in the reaction tube was 452° C. The position of the hot spot maximum in flow direction of the reaction gas was 90 cm beyond the start of section 2.

II. Repetition of the Partial Oxidation from C) I, but with Controlled Doping of the Fixed Catalyst Bed Introduced into the Thermal Tube with a Tandem Adhering Pair Obtained in the Course of Removal of Adhering Pairs in the Preparation of the Annular Coated Catalysts from Section 2 (the Total Amount of the Adhering Pairs Removed was 0.3% by Weight)

The fixed catalyst bed was charged as in C) I. In flow direction of the reaction gas, 90 cm beyond the start of section 2, however, a section 2 tandem adhering pair (0.092% by weight based on the total weight of coated catalysts introduced over all into the thermal tube) was positioned between the inner wall of the thermal tube and the outer wall of the thermowell such that its longitudinal axis pointed in the flow direction of the reaction gas. Otherwise, the procedure was as in C) I and the thermal tube charge was also conducted to the end in the same way.

With an unchanged position of the hotspot temperature, it increased to 463° C.

U.S. Provisional Patent Application No. 60/944,327, filed Jun. 15, 2007, is incorporated into the present patent application by literature reference. With regard to the above-mentioned teachings, numerous changes and deviations from the present invention are possible. It can therefore be assumed that the invention, within the scope of the appended claims, can be performed differently from the way described specifically herein.

The invention claimed is:

1. A process for introducing a portion withdrawn from at least one production charge of annular coated catalysts K into a reaction tube of a tube bundle reactor for the purpose of charging this reaction tube with a fixed catalyst bed suitable for performing a heterogeneously catalyzed partial gas phase oxidation of an organic starting compound, which comprises, before the withdrawal of the portion from the at least one production charge and/or after the withdrawal but before the introduction of the portion withdrawn into the reaction tube, removing fused adhering pairs of annular coated catalysts K formed in the preparation of the at least one production charge of annular coated catalysts K at least partly from the at least one production charge and/or from the portion withdrawn.

2. The process according to claim 1, wherein the coated catalysts K consist of an annular shaped support body and a coating of active composition applied thereto, from 4 to 10 mm, its height from 2 to 10 mm and its wall thickness from 1 to 4 mm.

3. The process according to claim 2, wherein the active composition comprises at least one multielement oxide.

4. The process according to claim 3, wherein the multielement oxide is one which comprises
  a) the elements Mo, Fe and Bi, or
  b) the elements Mo and V, or
  c) the element V and additionally P and/or Ti.

5. The process according to any of claims 1 to 4, wherein the fused adhering pairs are removed by a process for screening with the aid of a screen.

6. A process for introducing a portion withdrawn from at least one production charge of annular coated catalysts K into a reaction tube of a tube bundle reactor for the purpose of charging this reaction tube with a fixed catalyst bed suitable for performing a heterogeneously catalyzed partial gas phase oxidation of an organic starting compound, which comprises, before the withdrawal of the portion from the at least one production charge and/or after the withdrawal but before the introduction of the portion withdrawn into the reaction tube, removing adhering pairs of annular coated catalysts K formed in the preparation of the at least one production charge of annular coated catalysts K at least partly from the at least one production charge and/or from the portion withdrawn, wherein the adhering pairs are removed by a process for screening with the aid of a screen, and wherein, between the external diameter E and the height H of the annular coated catalyst K, the relationship $H \leq 0.5 \cdot E$ is satisfied and the screen has screen orifices $O_1$ within whose continuous outline a rectangle R with the side lengths L and C can be inscribed with the proviso $M_1$, $$L > E \geq 2H > C > H,$$

but not with the proviso $M_1^*$, $$L > C \geq 2H.$$

7. A process for introducing a portion withdrawn from at least one production charge of annular coated catalysts K into a reaction tube of a tube bundle reactor for the purpose of charging this reaction tube with a fixed catalyst bed suitable for performing a heterogeneously catalyzed partial gas phase oxidation of an organic starting compound, which comprises, before the withdrawal of the portion from the at least one production charge and/or after the withdrawal but before the introduction of the portion withdrawn into the reaction tube, removing adhering pairs of annular coated catalysts K formed in the preparation of the at least one production charge of annular coated catalysts K at least partly from the at least one production charge and/or from the portion withdrawn, wherein the adhering pairs are removed by a process for screening with the aid of a screen, and wherein, between the external diameter E and the height H of the annular coated catalyst K, the relationship $E \geq H > 0.5 \cdot E$ is satisfied and the screen has screen orifices $O_3$ within whose continuous outline a rectangle R with the side lengths L and C can be inscribed with the proviso $M_3$, $$L > E < 2H > C > H,$$

but not with the proviso $M_3^*$, $$L \geq C \geq 2H.$$

8. The process according to claim 6, wherein the screen orifice $O_1$ is a rectangle with the side lengths L and C.

9. The process according to claim 7, wherein the screen orifice $O_3$ is a rectangle with the side lengths L and C.

10. The process according to claim 6, wherein the screen orifice $O_1$ is an elongated hole which derives from a rectangle with the side lengths L and C.

11. The process according to claim 7, wherein the screen orifice $O_3$ is an elongated hole which derives from a rectangle with the side lengths L and C.

12. The process according to claim 1, which is followed by a process for heterogeneously catalyzed partial gas phase oxidation of an organic starting compound in the reaction tube charged with the fixed catalyst bed.

13. The process according to claim 12, wherein the heterogeneously catalyzed partial gas phase oxidation is the gas phase oxidation of acrolein to acrylic acid or the gas phase oxidation of o-xylene and/or naphthalene to phthalic anhydride.

14. A process for preparing annular coated catalysts by applying a catalytic active composition to annular shaped support bodies with the aid of a liquid binder, which comprises, after the preparation process has ended, at least partly removing fused adhering pairs of coated catalyst rings formed in the preparation.

15. A process for charging reaction tubes in a tube bundle reactor with a fixed catalyst bed, which comprises charging with annular coated catalysts which have been prepared by a preparation process according to claim 14.

16. A process according to claim 14, which is followed by a process comprising enveloping a portion of shaped catalyst bodies with a packing medium.

17. The process according to claim 6, wherein proviso $M_1$ is $$2E > L > E \geq 2H > C > H.$$

18. The process according to claim 6, wherein proviso $M_1$ is $$1.9E > L > E \geq 2H > C > H.$$

19. The process according to claim 6, which satisfies the following proviso $M_2$:

$$2E > L > E \geq 2H > 1.75H \geq C \geq 1.25H.$$

20. The process according to claim 6, which satisfies the following proviso $M_2$:

$$1.9E > L > E \geq 2H > 1.75H \geq C \geq 1.25H.$$

21. The process according to claim 7, which satisfies the following proviso $M_4$:

$$2E > L > E < 2H > C > H,$$

but not the proviso $M_4^*$:

$$L \geq C \geq 2H.$$

22. The process according to claim 7, which satisfies the following proviso $M_5$:

$$2H > L > E < 2H > C > H,$$

but not the proviso $M_5^*$:

$$L \geq C \geq 2H.$$

23. The process according to claim 6, which is followed by a process for heterogeneously catalyzed partial gas phase oxidation of an organic starting compound in the reaction tube charged with the fixed catalyst bed.

24. The process according to claim 23, wherein the heterogeneously catalyzed partial gas phase oxidation is the gas phase oxidation of acrolein to acrylic acid or the gas phase oxidation of o-xylene and/or naphthalene to phthalic anhydride.

25. The process according to claim 7, which is followed by a process for heterogeneously catalyzed partial gas phase oxidation of an organic starting compound in the reaction tube charged with the fixed catalyst bed.

26. The process according to claim 25, wherein the heterogeneously catalyzed partial gas phase oxidation is the gas phase oxidation of acrolein to acrylic acid or the gas phase oxidation of o-xylene and/or naphthalene to phthalic anhydride.

27. A process for preparing annular coated catalysts by applying a catalytic active composition to annular shaped support bodies with the aid of a liquid binder, which comprises, after the preparation process has ended, at least partly removing adhering pairs of coated catalyst rings formed in the preparation, wherein the adhering pairs are removed by a process for screening with the aid of a screen, and wherein, between the external diameter E and the height H of the annular coated catalyst, the relationship H≦0.5·E is satisfied and the screen has screen orifices $O_1$ within whose continuous outline a rectangle R with the side lengths L and C can be inscribed with the proviso $M_1$, $$L>E\geq 2H>C>H,$$

but not with the proviso $M_1^*$, $$L>C\geq 2H.$$

28. A process for charging reaction tubes in a tube bundle reactor with a fixed catalyst bed, which comprises charging with annular coated catalysts which have been prepared by a preparation process according to claim 27.

29. A process according to claim 27, which is followed by a process comprising enveloping a portion of shaped catalyst bodies with a packing medium.

30. A process for preparing annular coated catalysts by applying a catalytic active composition to annular shaped support bodies with the aid of a liquid binder, which comprises, after the preparation process has ended, at least partly removing adhering pairs of coated catalyst rings formed in the preparation, wherein the adhering pairs are removed by a process for screening with the aid of a screen, and wherein, between the external diameter E and the height H of the annular coated catalyst K, the relationship E≧H>0.5·E is satisfied and the screen has screen orifices $O_3$ within whose continuous outline a rectangle R with the side lengths L and C can be inscribed with the proviso $M_3$, $$L>E<2H>C>H,$$

but not with the proviso $M_3^*$, $$L\geq C\geq 2H.$$

31. A process for charging reaction tubes in a tube bundle reactor with a fixed catalyst bed, which comprises charging with annular coated catalysts which have been prepared by a preparation process according to claim 30.

32. A process according to claim 30, which is followed by a process comprising enveloping a portion of shaped catalyst bodies with a packing medium.

* * * * *